(12) United States Patent
Hawkins et al.

(10) Patent No.: US 8,859,220 B2
(45) Date of Patent: *Oct. 14, 2014

(54) LUCIFERASE-BASED ASSAYS

(71) Applicant: Promega Corporation, Madison, WI (US)

(72) Inventors: Erika Hawkins, Madison, WI (US); James J. Cali, Verona, WI (US); Samuel Kin Sang Ho, New Bedford, MA (US); Martha A. O'Brien, Madison, WI (US); Richard Somberg, Madison, WI (US); Robert F. Bulleit, Verona, WI (US); Keith V. Wood, Mount Horeb, WI (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/750,293

(22) Filed: Jan. 25, 2013

(65) Prior Publication Data

US 2013/0217052 A1    Aug. 22, 2013

Related U.S. Application Data

(62) Division of application No. 12/819,334, filed on Jun. 21, 2010, now Pat. No. 8,361,739, which is a division of application No. 10/746,995, filed on Dec. 23, 2003, now Pat. No. 7,741,067.

(60) Provisional application No. 60/447,334, filed on Feb. 13, 2003, provisional application No. 60/444,264, filed on Jan. 31, 2003, provisional application No. 60/436,173, filed on Dec. 23, 2002.

(51) Int. Cl.
*C12Q 1/66* (2006.01)
*C12Q 1/34* (2006.01)
*C12Q 1/48* (2006.01)

(52) U.S. Cl.
CPC .......................................... *C12Q 1/66* (2013.01)
USPC ................................... 435/8; 435/15; 435/21

(58) Field of Classification Search
None
See application file for complete search history.

(56) References Cited

U.S. PATENT DOCUMENTS

| | | | |
|---|---|---|---|
| 4,390,274 A | 6/1983 | Berthold et al. | |
| 4,906,565 A | 3/1990 | Vossen | |
| 5,165,935 A | 11/1992 | Andre et al. | |
| 5,283,179 A | 2/1994 | Wood | |
| 5,587,286 A | 12/1996 | Pahuski et al. | |
| 5,618,682 A | 4/1997 | Scheirer | |
| 5,648,232 A | 7/1997 | Squirrell | |
| 5,650,289 A | 7/1997 | Wood | |
| 5,670,356 A | 9/1997 | Sherf et al. | |
| 5,677,290 A | 10/1997 | Fukunaga | |
| 5,741,635 A | 4/1998 | Boss et al. | |
| 5,744,320 A | 4/1998 | Sherf et al. | |
| 5,866,348 A | 2/1999 | Scheirer | |
| 6,235,480 B1 | 5/2001 | Shultz et al. | |
| 6,319,898 B1 | 11/2001 | Davies et al. | |
| 6,599,711 B2 | 7/2003 | Crouch et al. | |
| 6,911,319 B2 | 6/2005 | Crouch et al. | |
| 7,083,911 B2 | 8/2006 | Wood et al. | |
| 7,148,030 B2 | 12/2006 | O'Brien et al. | |
| 7,700,310 B2 * | 4/2010 | Somberg et al. | ................ 435/15 |
| 7,741,067 B2 | 6/2010 | Hawkins et al. | |
| 8,361,739 B2 | 1/2013 | Hawkins et al. | |
| 2003/0104507 A1 | 6/2003 | Wood et al. | |
| 2003/0153090 A1 | 8/2003 | Wood et al. | |
| 2004/0101922 A1 | 5/2004 | Somberg et al. | |
| 2004/0171099 A1 | 9/2004 | Cali et al. | |
| 2004/0253658 A1 | 12/2004 | Crouch et al. | |
| 2013/0217051 A1 | 8/2013 | Hawkins et al. | |

FOREIGN PATENT DOCUMENTS

| | | |
|---|---|---|
| DE | 68905373 | 3/1993 |
| DE | 3786279 | 6/1993 |
| DE | 68912950 | 2/1994 |
| DE | 69409830 | 4/1998 |
| DE | 69412790 | 8/1998 |
| EP | 0022432 | 1/1981 |
| EP | 0610937 | 8/1994 |
| EP | 1041151 | 10/2000 |
| JP | 03-251199 | 11/1991 |
| JP | 7-203995 | 8/1995 |
| JP | 9-107994 | 4/1997 |
| JP | 10-165200 | 6/1998 |
| JP | 11-332593 | 12/1999 |
| JP | 2012-105676 | 6/2012 |
| WO | WO 92/04468 | 3/1992 |
| WO | WO 94/17202 | 8/1994 |

(Continued)

OTHER PUBLICATIONS

Aiginger et al., J. Clin. Chem. Clin. Biochem. (1980) 1:216.
Alexandre, I. et al., "Comparison of three luminescent assays combined with a sandwich hybridization for the measurement of PCR-amplified human cytomegalovirus DNA," J. Virological Methods (1997) 66:113-123.
Andreotti, P.E. et al., "Chemosensitivity testing of human tumors using a microplate adenosine triphosphate luminescence assay; clinical correlation for cisplatin resistance of ovarian carcinoma," Cancer Res. (1995) 55(22):5276-5282.
Ausubel et al., Current Protocols in Molecular Biology, Wiley Inter-Science, New York, pp. 1.6.2-1.6.4 (1997).

(Continued)

*Primary Examiner* — Jon P Weber
*Assistant Examiner* — Charles Zoltan Constantine
(74) *Attorney, Agent, or Firm* — Michael Best & Friedrich LLP

(57) ABSTRACT

A method and kit are provided for enhancing the tolerance of an assay reagent to compounds in an assay sample, the assay reagent including a luciferase enzyme. The method includes contacting the luciferase with a tolerance enhancement agent in an amount sufficient to substantially protect luciferase enzyme activity from interference of the compound and minimize interference by at least about 10% relative to an assay not having tolerance enhancement agent.

15 Claims, 6 Drawing Sheets

(56) References Cited

FOREIGN PATENT DOCUMENTS

| | | |
|---|---|---|
| WO | WO 95/16202 | 6/1995 |
| WO | WO 96/40988 | 12/1996 |
| WO | WO 97/48803 | 12/1997 |
| WO | WO 98/37096 | 8/1998 |
| WO | WO 98/39444 | 9/1998 |
| WO | WO 99/09199 | 2/1999 |
| WO | WO 99/14336 | 3/1999 |
| WO | WO 99/26657 | 6/1999 |
| WO | WO 99/38999 | 8/1999 |
| WO | WO 00/18953 | 4/2000 |
| WO | WO 00/50631 | 8/2000 |
| WO | WO 01/20002 | 3/2001 |
| WO | WO 01/96862 | 12/2001 |
| WO | WO 02/48390 | 6/2002 |
| WO | WO 0248390 A2 * | 6/2002 |
| WO | WO 02/066671 | 8/2002 |
| WO | WO 2004/059294 | 7/2004 |

OTHER PUBLICATIONS

Babcock, J. et al., "Automated nonisotopic assay for protein-tyrosine kinase and protein-tyrosine phosphatase activities," Anal. Biochem. (1991) 196(2):245-251.

Bachy, M. et al., "Beta galactosidase release as an alternative to chromium release in cytotoxic T-cell assays," J. Immunol. Methods (1999) 230:37-46.

Baldwin, T.O. et al., "Purification of firefly luciferase from recombinant sources," Methods in Enzymology (2000) 305:180-188.

Beny, M. et al., "Separation of firefly luciferase using an anion exchanger," FEBS Letters (1976) 70(1):167-70.

Bessho, M. et al., "Assay of rat plasma pyruvate activity with luciferin-luciferase," J. Nutri. Sci. Vitaminol. (1988) 34:607-614.

Bowie, L.J. et al., "Synthesis of a new substrate analog of firefly luciferin. An active-site probe," Biochem. (1973) 12(10:1845-1852.

Bradbury, D.A. et al., "Measurement of the ADP:ATP ratio in human leukaemic cell lines can be used as an indicator of cell viability, necrosis and apoptosis," J. Immunol. Methods (2000) 240(1-2):79-92.

Branchini, B.R. et al., "A convenient affinity chromatography-based purification of firefly luciferase," Anal. Biochem. (1980) 104(2):386-396.

Branchini, B.R. et al., "Chemical synthesis of firefly luciferin analogs and inhibitors," Methods Enzymol. (2000) 305:188-195.

Branchini, B.R. et al., "Naphthyl- and quinolylluciferin: green and red light emitting firefly luciferin analogues," protochem. Photobiol. (1989) 49(5):689-695.

Branchini, B.R. et al., "Site-directed mutagenesis of firefly luciferase active site amino acids: a proposed model for bioluminescence color," Biochem. (1999) 38:13223-13230.

Branchini, B.R. et al., "The role of lysine 529, a conserved residue of the acyl-adenylate-forming enzyme superfamily, in firefly luciferase," Biochem. (2000) 39:5433-5440.

Briggs, S.D. et al., "Affinity of Src family kinase SH3 domains for HIV nef in vitro does not predict kinase activation by nef in vivo," Biochem. (2000) 39(3):489-495.

Brolin, S.E. et al., "Design of coupled reactions for simplification of bioluminescence analysis," J. Biolum. Chemilumi. (1989) 4:446-453.

Bronstein, I. et al., "Chemiluminescent and bioluminescent reporter gene assays," Anal. Biochem. (1994) 219:169-181.

Brovko, L.Yu. et al., "Use of immobilized firefly luciferase for quantative determination of ATP and enzymes that synthesize and destroy ATP," Biokhimiya (1978) 43(5):798-805.

Builder, S.E. et al., "The mechanism of activation of bovine skeletal muscle kinase by adenosine 3':5' monophosphate," J. Biol. Chem. (1980) 255(8):3514-3519.

Carter, P., "Site-directed mutagenesis," Biochem. J. (1986) 237(1):1-7.

Cho, L.C. et al., "To lap or not to lap," The Oncologist (1996) 1:120-124.

Cohen, C.B. et al., "A microchip-based enzyme assay for protein kinase A," Anal. Biochem. (1999) 273:89-97.

Cox, B. et al., "Application of high-throughput screening techniques to drug discovery," Progress in Medicinal Chemistry, Edited by F.D. King and A.W. Oxford (2000) vol. 37, Chapter 3, pp. 83-133, Amsterdam, Netherlands.

Craig, F.F. et al., "Membrane-permeable luciferin esters for assay of firefly luciferase in live intact cells," Biochem. J. (1991) 276(3):637-641.

Cree and Adreotti, "Methotrexate chemosensitivity by ATP luminescence in human leukemia cell lines and in breast cancer primary cultures: comparison of the TCA-100 assay with a clonogenic assay," Anti-cancer Drugs (1995) 6(3):398-404.

Crouch, S.P. et al., "The use of ATP bioluminescence as a measure of cell proliferation and cytotoxicity," J. Immunol. Methods (1993) 160(1):81-88.

D'Atri, S. et al., "A miniaturized cell-mediated cytotoxicity assay with human effector mononuclear cells," Int. J. Tiss. Reac. (1986) VIII(5):383-390.

Decker, T. et al., "A quick and simple method for the quantitation of lactate dehydrogenase release in measurements of cellular cytotoxicity and tumor necrosis factor (TNF) activity," J. Immunol. Meth. (1988) 25:61-69.

Devine, J.H. et al., "Luciferase from the East Europe firefly *Luciola mingrelica*: cloning and nucleotide sequence of the cDNA, overexpression in *Escherichia coli* and purification of the enzyme," Biochemica et Biophysica Acta (1993) 1173:121-132.

Dukhovich, A.F. et al., "Significance of lipids for the functioning of firefly luciferase: kinetic mechanism of delipidation of the enzyme," Biokhimiya (1987) 52(8):1364-1372.

Eriksson, J. et al., "Method for real-time detection of inorganic pyrophosphatase activity," Analytical Biochem. (2001) 293:67-70.

Eu, J-Y. et al., "Homogeneous bioluminescnece assay for galactosuria: interference and kinetic analysis," Analytical Biochem. (1999) 271:168-176.

Fan, F. et al., "Bioluminescent assays for high-throughput screening," Assay and Drug Development Technologies (2007) 5(1):127-136.

Feng, B.Y. et al., "High-throughput assays for promiscuous inhibitors," Nature Chem. Biol. (2005) 1(3):146-148.

Feng, B.Y. et al., "A detergent-based assay for the detection of promiscuous inhibitors," Nature Protocols (2006) 1(2):550-553.

Filippova, N.Y. et al., "New approaches to the preparation and application of firefly luciferase," J. Biolumin. Chemilum. (1989) 4(1):419-422.

Finegan, B.A. et al., "Comparison of the haemodynamic effects of adenosine monophosphate with sodium nitroprusside in a canine model of acute global left ventricular dysfunction," Br. J. Pharmacol. (1991) 103:1691-1696.

Flanagan, W.M., "Analysis of the herpes smplex virus type 1 promoter controlling the expression of UL38, a true late gene involved in capsid assembly," J. Virol. (1991) 65(2):769-786.

Garraud et al., "Effect of blood storage on lymphocyte subpopulations," J. Immun. Meth. (1984) 75:85-94.

Glass, D.B. et al., "Comparison of the substrate specificity of adenosine 3':5'-monophosphate- and guanosine 3':5'-monophoshphate-dependent protein kinases. Kinetic studies using synthetic peptides corresponding to phosphorylation sites in histone H2B," J. Biol. Chem. (1979) 254(19):9728-9738.

Golding, E.M. et al., "Adjustment of K' to varying pH and pMg for the creatine kinase, adenylate kinase and ATP hydrolysis equilibria permitting quantitive bioenergetic assessment," J. Experimental Biol. (1995) 198:1775-1782.

Gonzalez, A. et al., "Use of the synthetic peptide neurogranin as a selective protein kinase C substrate in assyas of tissue homogenates," Analytical Biochem. (1993) 215:184-189.

Handa, A.K. et al., "Assay of adenosine 3', 5' cyclic monophosphate by stimulation of protein kinase: a method not involving radioactivity," Anal. Biochem. (1980) 102:332-339.

Handa, A.K. et al., "Cyclic adenosine 3':5'-monophosphate in moss protonema," Plant Physiol. (1977) 59:490-496.

Hanocq-Quertier, J. et al., "Bioluminiscent assay of ATPase activity in embryonic material using firefly luciferase," J. Biolum. Chemilumin. (1988) 2:17-24.

(56) References Cited

OTHER PUBLICATIONS

Hart et al., "*Renilla reniformis* bioluminescence: luciferase-catalyzed production of nonradiating excited states from luciferin analogues and elucidation of the excited state species involved in energy transfer to *Renilla* green fluorescent protein," Biochem. (1979) 18(11):2204-2210.
Hastings, J.W. et al., "Bioluminescence and chemiluminescence," Protochem. Photobiol. (1976) 23(6):461-473.
Hastings, J.W., "Chemistries and colors of bioluminescent reactions. A review," Gene (1996) 173:5-11.
Idahl, I-A. et al., "Measurements of serum glucose using the luciferin/luciferase system and a liquid scintillation spectrometer," Anal. Biochem. (1986) 155:177-181.
Inouye, S. et al., "The use of *Renilla* luciferase, oplophorus luciferase and apoaequorin as bioluminescent reporter protein in the presence of coelenterazine analogues as substrate," Biochem. Biophys. Res. Commun. (1997) 233:349-353.
Jain, V.K. et al., "Dual reporter vectors for determination of activity of bidirectional promoters," Biotechniques (1992) 12(5):681-684.
Jones, K., "Glowing jellyfish, luminescence and a molecule called coelenterazine," Trends Biotech. (1999) 17(12):477-481.
Kangas et al., "Bioluminescence of cellular ATP: a new method for evaluating cytotoxic agents in vitro," Med. Biol. (1984) 62(6):338-343.
Kapoor, M. et al., "Pyruvate kinase of *Neurospora crassa*: effect of various ligands on the rate of inactivation by protein denaturants," Can. J. Microbiol. (1972) 18(8):1221-1232.
Karamohamed, S. et al., "Real-time bioluminometric method for detectino of nucleoside diphosphate kinase activity," Biotech. (1999) 26:728-734.
Karamohamed, S. et al., "Real-time detection and quantification of adenosine triphosphate sulfurylase activity by a bioluminometric approach," Anal. Biochem. (1999) 271:81-85.
Karp, M. et al., "A streptavidin-luciferase fusion protein: comparisons and applications," Biomol. Eng. (1999) 16:101-104.
Kasatori, N. et al., "Cytotoxity test based on luminescent assay of alkaline phosphate released from target cells," Japan J. Clin. Pathol. (1994) 42:1050-1054.
Khokhlatchev, A. et al., "Reconstitution of mitogen-activated protein kinase phosphorylation cascades in bacteria," J. Biol. Chem. (1997) 272(17):11057-11062.
Kiechle et al., "Isolation from rat adipocytes of a chemical mediator for insulin activation of pyruvate dehydrogenase," Diabetes (1980) 29(10):852-855.
Kuo, J-F. et al., "An assay method for cyclic AMP and cyclic GMP based upon their abilities to activate cyclic AMP-dependent and cyclic GMP-dependent protein kinases," Adv. Cyclic Nucleotide Res. (1972) 2:41-50.
Leckie, F. et al., "Normalization of GUS by luciferase activity from the same cell extract reduces transformation variability," Biotechniques (1994) 17(1):52-3, 56-7.
Lehel, C. et al., "A chemiluminescent microtiter plate assay for sensitive detectino of protein kinase activity," Anal. Biochem. (1997) 244:340-346.
Lev, S. et al., "A specific combination of substrates is involved in signal transduction by the kit-encoded receptor," EMBO Journal (1991) 10:647-654.
Lundin, A. et al., "Continuous monitoring of ATP-converting reactions by purified firefly luciferase," Anal. Biochem. (1976) 75:611-620.
McDonald, O.B. et al., "A scintillation proximity assay for the Raf\MEK\ERK kinase cascade: high-throughout screening and identification of selective enzyme inhibitors," Anal. Biochem. (1999) 268:318-329.
McElroy, M.B., "Models for the nighttime venus ionosphere," J. Geophys. Res. (1969) 74(5):1118-1127.
Meisenheimer, P.L. et al., "Luminogenic enzyme substrates: the basis for a new paradigm in assay design," Promega Cell Notes (2008) Issue 22, pp. 10-14.
Miska, W. et al., "Synthesis and characterization of luciferin derivatives for use in bioluminescence enhanced enzyme immunoassays. New ultrasensitive detection systems for enzyme immunoassays, I," J. Clin. Chem. Clin. Biochem. (1987) 25(1):23-30.
Moyer, J.D. et al., "Nucleoside triphosphate specificity of firefly luciferase," Anal. Biochem. (1983) 131(1):187-189.
Naslund, B. et al., "Luminometric single step urea assay using ATP-hydrolyzing urease," Clin. Chem. (1998) 44(9):1964-1973.
Nguyen, V.T. et al., "Firefly luciferase luminescence assays using scintillation counters for quantitation in transfected mammalian cells," Anal. Biochem. (1988) 171(2):404-408.
Nociari, M.M. et al., "A novel one-step, highly sensitive fluorometric assay to evaluate cell-mediated cytotoxicity," J. Immunol. Meth. (1998) 213:157-167.
Olsson, T. et al., "Leakage of adenylate kinase from stored blood cells," J. Appl. Biochem. (1983) 5:437-445.
Parsons, S.J.W. et al., "Use of a dual firefly and *Renilla* luciferase reporter gene assay to simultaneously determine drug selectivity at human corticotrophin releasing hormone 1 and 2 receptors," Anal. Biochem. (2000) 281:187-192.
Pastorino, J.G. et al., "Functional consequences of the sustained or transient activation by Bax of the mitochondrial permeability transition pore," J. Biol. Chem. (1999) 274(44):31734-31739.
Pereira, D.A. et al., "Review: historical perspectives in pharmacology. Origin and evolution of high throughput screening," Br. J. Pharmacol. (2007) 152:53-61.
Picciolo, G.L. et al., "Performance characteristics of a new photometer with a moving filter tape for aluminescence assay," Appl. Environ. Micriobiol. (1977) 34(6):720-724.
Promega Corporation Technical Bulletin No. 318, "Kinase-Glo™ Luminscent Kinase Assay," Dec. 2002, 12 pages.
Robbins, D.J. et al., "Regulation and properties of extracellular signal-regulated protein kinases 1 and 2 in vitro," J. Biol. Chem. (1993) 268(7):5097-5106.
Ronner, P. et al., "Luminometric assays of ATP, phosphocreatine and creatine for estimation of free ADP and free AMP," Anal. Biochem. (1999) 275(2):208-216.
Ryan, A.J. et al., "Effect of detergent on pomiscuous inhibitors," J. Med. Chem. (2003) 46:3448-3451.
Sala-Newby, G. et al., "Engineering firefly luciferase as an indicator of cyclic AMP-dependent protein kinase in living cells," FEBS (1992) 307(2):241-244.
Sambrook, Molecular Cloning: A Laboratory Manual, Cold Spring Harbor Laboratory Press, Cold Spring Harbor, New York (1969).
Seethala, R. et al., "A fluorescence polarization competition immunoassay for tyrosine kinases," Anal. Biochem. (1998) 255:257-262.
Seethala, R. et al., "A homogenous, fluorescence polarization assay for Src-family tyrosine kinases," Anal. Biochem. (1997) 253(2):210-218.
Seger, R. et al., "Purification and characterization of mitogen-activated protein kinases activator(s) from epidermal growth factor-stimulated A 431 cells," J. Biol. Chem. (1992) 267(20):14373-14381.
Shimomura, O. et al., "Semi-synthetic aequorins with improved sensitivity to Ca2+ ions," Biochem. J. (1989) 261:913-920.
Simpson, W.J. et al., "The effect of detergents on firefly luciferase reactions," J. Bioluminescence and Chemiluminescence (1991) 6:97-106.
Tatsumi, H. et al., "Construction of biotinylated firefly using biotin acceptor peptides," Anal. Biochem. (1996) 243:176-180.
Teague, W.E. et al., "Adjustment of K' for the creatine kinase, adenylate kinase and ATP hydrolysis equilibria to varying temperature and ionic strength," J. Exp. Biol. (1996) 199:509-512.
Teranishi, K. et al., "Coelenterazine analogs as chemiluminescent probe for superoxide anion," Anal. Biochem. (1997) 249:37-43.
Thomson, C.M., "The widespread occurrence and tissue distribution of the imidazolopyrazine luciferins," J. Biolumin. Chemilumin. (1997) 12(2):87-91.
Thore, A. "Technical aspects of the bioluminescent firefly luciferase assay of ATP," Science Tools (1979) 26(2):30-34.
Ugarova, N.N. et al., "Bioluminescent assay of creatine kinase activity using immobilized firefly extract," Anal. Biochem. (1986) 158:1-5.

(56) References Cited

OTHER PUBLICATIONS

Von Ahsen, O. et al., "High-throughput screening for kinase inhibitors," ChemBioChem. (2005) 6:481-490.
Wells, J.A. et al., "Cassette mutagenesis: an efficient method for generation of multiple mutations at defined sites," Gene (1985) 34(2-3):315-323.
White, E.H. et al., "Chemi- and bioluminescence of firefly luciferin," J. Am. Chem. Soc. (1969) 91(8):2178-2180.
White, E.H. et al., "Modification of firefly luciferase with a luciferin analog. A red light producing enzyme," J. Am. Chem. Soc. (1975) 97(5):1243-1245.
White, P.J. et al., "Improved thermostability of the North American firefly luciferase: saturation mutagenesis at position 354," Biochem. J. (1996) 319:343-350.
Wood, K.V. et al., "Complementary DNA coding click beetle luciferases can elicit bioluminescence of different colors," Science (1989) 244(4905):700-702.
Wood, K.V. et al., "Introduction to beetle luciferases and their applications," J. Biolumin. Chemilumin. (1989) 4(1):289-301.
Yang, J. et al., "An easily synthesized, photolyzable luciferase substrate for in vivo luciferase activity measurement," Biotechniques (1993) 15(5):848-850.
Zoller, M.J. et al., "Oligonucleotide-directed mutagenesis: a simple method using two oligonucleotide primers and a single-stranded DNA template," Methods Enzymol. (1987) 154:329-350.
Australian Patent Office Action for Application No. 2003300008 dated Jul. 4, 2006 (1 page).
Canadian Patent Office Action for Application No. 2508072 dated Nov. 18, 2008 (7 pages).
Canadian Patent Office Action for Application No. 2508072 dated Aug. 2, 2010 (3 pages).
European Patent Office Examination Report for Application No. 03800272.1 dated Aug. 22, 2007 (8 pages).
European Patent Office Supplemental Search Report for Application No. 03800272.1 dated Jan. 17, 2007 (3 pages).
European Patent Office Action for Application No. 03800272.1 dated Aug. 4, 2008 (4 pages).
European Patent Office Action for Application No. 03800272.1 dated Mar. 11, 2009 (4 pages).
European Patent Office Action for Application No. 03800272.1 dated Jan. 14, 2010 (5 pages).
European Patent Office Action for Application No. 03800272.1 dated Sep. 30, 2010 (8 pages).
European Patent Office Action for Application No. 03800272.1 dated Sep. 13, 2011 (6 pages).
European Patent Office Action for Application No. 03800272.1 dated Jul. 30, 2012 (4 pages).
European Patent Office Action for Application No. 10075527.1 dated Apr. 21, 2011 (9 pages).
European Patent Office Action for Application No. 10075525.5 dated Apr. 20, 2011 (10 pages).
European Patent Office Action for Application No. 10075527.1 dated Dec. 28, 2011 (6 pages).
Japanese Patent Office Action for Application No. 2005-510073 dated Jul. 28, 2009 (6 pages).
Japanese Patent Office Action for Application No. 2005-510073 dated Nov. 20, 2007 (19 pages).
Japanese Patent Office Action for Application No. 2008-129504 dated Jul. 27, 2010 (10 pages) with English translation.
Japanese Patent Office Action for Application No. 2008-129504 dated Nov. 2, 2011 (6 pages).
Japanese Patent Office Action for Application No. 2009-272379 dated Oct. 6, 2011 (7 pages) with English translation.
Japanese Patent Office Action for Application No. 2009-272379 dated Sep. 20, 2012 (5 pages) with English translation.
International Search Report for Application No. PCT/US03/41454 dated May 4, 2006 (3 pages).
International Preliminary Examination Report for Application No. PCT/US03/41454 dated Dec. 7, 2006 (6 pages).
United States Patent Office Action for U.S. Appl. No. 10/746,995 dated Aug. 25, 2006 (9 pages).
United States Patent Office Action for U.S. Appl. No. 10/746,995 dated Jun. 18, 2007 (12 pages).
United States Patent Office Action for U.S. Appl. No. 10/746,995 dated Oct. 17, 2007 (2 pages).
United States Patent Office Action for U.S. Appl. No. 10/746,995 dated Feb. 6, 2008 (7 pages).
United States Patent Office Action for U.S. Appl. No. 10/746,995 dated Sep. 3, 2008 (7 pages).
United States Patent Office Notice of Allowance for U.S. Appl. No. 12/819,334 dated Sep. 21, 2012 (51 pages).
European Patent Office Action for Application No. 03800272.1 dated Feb. 18, 2013 (6 pages).
Kondepudi, A. et al., "A chemiluminescent transcription reporter assay utilizing genes encoding two distinct secreted phosphatases," Poster Abstract #725 presented at annual meeting of the American Society of Cell Biologists, Dec. 10-14, 1994, San Francisco, California.
Wilson, T. et al., "Bioluminescence," Annu. Rev. Cell Dev. Biol. (1998) 14:197-230.
McGovern et al. "A Specific Mechanism of Nonspecific Inhibition" Journal of Medicinal Chemistry 2003, vol. 46, 4265-4272.
United States Patent Office Notice of Allowance for U.S. Appl. No. 13/750,284 dated Jul. 31, 2013 (13 pages).
Japanese Patent Office Action for Application No. 2008-129504 dated Oct. 3, 2013 (6 pages) with English translation.

\* cited by examiner

LUCIFERASE-BASED ASSAYS

CROSS-REFERENCE

This application is a divisional of U.S. application Ser. No. 12/819,334 filed Jun. 21, 2010, now U.S. Pat. No. 8,361,739 issued Jan. 29, 2013, which is a divisional of U.S. application Ser. No. 10/746,995 filed Dec. 23, 2003, now U.S. Pat. No. 7,741,067 issued Jun. 22, 2010, which claims the benefit of priority to U.S. Provisional Application Nos. 60/447,334 filed Feb. 13, 2003, 60/444,264 filed Jan. 31, 2003, and 60/436,173 filed Dec. 23, 2002, the disclosures of each of which are incorporated by reference herein in their entirety for any purpose. Priority to each application is hereby claimed.

FIELD OF THE INVENTION

The present invention relates generally to bioluminescence. More particularly, the invention concerns methods, compositions, and kits for improving the accuracy of luciferase-based assays for high throughput screening of compound libraries by reducing the number of "false hits". The invention is particularly well suited for assays and test kits which use bioluminescence for quantitating products or occurrences of certain biospecific reactions in cellular and cell-free systems.

BACKGROUND OF THE INVENTION

Advances in the biological, biomedical and pharmaceutical sciences have accelerated the pace of research and diagnostics to a level unparalleled to the past. With sequences of whole genome becoming available quickly and successively, the assembly of large libraries of small molecules, the ability to move pharmaceutical development, clinical diagnostic tests and basic research from a reductionist to a whole system approach quickly all demand assays that facilitate high throughput analyses. Molecules no longer need to be singly analyzed for their effects on a lone process. Instead, the effects of many molecules on several biological systems can be studied simultaneously if appropriate, fast, reliable, and accurate assays are available.

Efficient, reliable and accurate assays for determining the occurrence of a certain biospecific events, e.g., enzyme inhibition in a cell-free environment or for assessing cell viability can be used to rapidly discover potential new pharmaceutical agents and to determine the cytotoxic effect or cell proliferation effect of such agents on cells. For instance, cancer pharmaceutical research often endeavors to identify compounds that selectively kill rapidly dividing cells, a primary characteristic of cancer cells. High throughput screens of compound libraries, coupled with efficient cell viability assays, can swiftly identify such compounds as potential cancer drugs. The efficacy of a candidate compound on cell viability can be assayed by detecting ATP since ATP production is realized only in metabolically active live cells; residual ATP is rapidly degraded upon necrotic cell death. See U.S. patent application Ser. No. 09/813,279, filed Mar. 19, 2001, entitled "Improved Method for detection of ATP" (assignee: Promega) which is incorporated by reference in its entirety. In another example, the identification of potential drug compounds that should move forward in the drug development process can be made by determining the effects of these compounds on cytochrome P-450 enzyme activity. See U.S. application Ser. No. 10/665,314, filed Sep. 19, 2003, entitled "Luminescence-based methods and probes for measuring cytochrome P-450 activity" (assignee: Promega) which is incorporated by reference in its entirety. In a final example, proteases represent a large and important group of enzymes involved in diverse physiological processes including blood coagulation, inflammation, reproduction, fibrinolysis, and the immune response. The identification of protease inhibitors may be useful for the investigation, treatment or management of disease states caused by or characterized by the alteration in the activity of specific proteases. See U.S. Provisional application No. 60/353,158, filed Feb. 1, 2002 entitled "Bioluminescent Protease Assay" (assignee: Promega), which is incorporated by reference in its entirety. Assay systems like these not only facilitate the evaluation of a substance on cell viability or proliferation in a cellular environment or on the occurrence of a biospecific reaction, but also permit high throughput screens that can rapidly test thousands of compounds, streamlining new drug discovery.

The use of reporter molecules or labels to qualitatively or quantitatively monitor molecular events is well established in assays used for medical diagnosis, for the detection of toxins and other substances in industrial environments and for basic and applied research in biology, biomedicine and biochemistry. Reporter molecules or labels in such assay systems have included radioactive isotopes, fluorescent agents, enzymes, including light-generating enzymes such as luciferase. Desirable characteristics of any reporter molecule systems include safe, quick and reliable application and detection. Luminescent systems are among the most desirable since they are exceptionally safe and sensitive.

Light-emitting systems have been known and isolated from many luminescent organisms, including certain bacteria, protozoa, coelenterates, mollusks, fish, millipedes, flies, fungi, worms, crustaceans, and beetles. Those enzymes isolated from beetles, particularly the fireflies of the genera *Photinus*, *Photuris* and *Luciola* and click beetles of genus *Pyrophorus* have found widespread use in reporter systems. In many of these organisms, enzymatically catalyzed oxidoreductions take place in which the free energy change is utilized to excite a molecule to a high-energy state. When the excited molecule spontaneously returns to the ground state, visible light is emitted. This emitted light is called "bioluminescence" or "luminescence". Luminescent luciferase-based assays have been developed to monitor or measure kinase activity, P-450 activity, and protease activity. See, for instance, U.S. application Ser. No. 10/665,314, filed Sep. 19, 2003 (P-450 activity); U.S. patent application Ser. No. 09/813,279, filed Mar. 19, 2001 (kinase activity); and U.S. provisional application no. 60/353,158, filed Feb. 1, 2002 (protease activity), commonly owned by Promega Corporation.

Genetic reporter systems are widely used to study eukaryotic gene expression and cellular physiology. Applications include the study of receptor activity, transcription factors, intracellular signaling, mRNA processing and protein folding. Currently, luciferase genes from a wide variety of vastly different species, particularly the luciferase genes of *Photinus pyralis* (the common firefly of North America), *Pyrophorus plagiophthalamus* (the Jamaican click beetle), *Renilla reniformis* (the sea pansy), and several bacteria (e.g., *Xenorhabdus luminescens* and *Vibrio* spp), are extremely popular luminescence reporter genes. Reference is made to Bronstein, et al. (1994) Anal. Biochem., Vol. 219, pp. 73-82, for a review of luminescence reporter gene assays. Firefly luciferase is also a popular reporter for ATP concentrations, and in that role is widely used to detect biomass. Various other reporter applications of luciferases have been described in the scientific literature. Luminescence may be produced by other enzymes when mixed with certain synthetic substrates; such as alkaline phosphatase mixed with adamantyl dioxetanes, or horseradish peroxidase mixed with luminol.

Luciferase genes are widely used as genetic reporters due to the non-radioactive nature, sensitivity, and extreme linear range of luminescence assays. For instance, as few as $10^{-20}$ moles of the firefly luciferase can be detected. Consequently, luciferase assays of gene activity are used in virtually every experimental biological system, including both prokaryotic and eukaryotic cell cultures, transgenic plants and animals, and cell-free expression systems. Similarly, luciferase assays of ATP are highly sensitive, enabling detection to below $10^{-16}$ moles of ATP.

Luciferases generate light via the oxidation of enzyme-specific substrates, called luciferins. For firefly luciferase and all other beetle luciferases, this is done in the presence of magnesium ions, oxygen, and ATP. For anthozoan luciferases, including *Renilla* luciferase, only oxygen is required along with the luciferin. Generally, in luminescence assays of genetic activity, reaction substrates and other luminescence-activating reagents are introduced into a biological system suspected of expressing a reporter enzyme. Resultant luminescence, if any, is then measured using a luminometer or any suitable radiant energy-measuring device. The assay is very rapid and sensitive, and provides gene expression data quickly and easily, without the need for radioactive reagents. Reporter assays other than for genetic activity are performed analogously.

The conventional assay of genetic activity using firefly luciferase has been further improved by including coenzyme A (CoA) in the assay reagent to yield greater enzyme turnover and thus greater luminescence intensity. (Promega Luciferase Assay Reagent, Cat. No. E1500, Promega Corporation, Madison, Wis.; see U.S. Pat. No. 5,283,179, issued Feb. 1, 1994.) Using this reagent, luciferase activity can be readily measured in luminometers or scintillation counters. The luciferase reaction, modified by the addition of CoA to produce persistent light emission, provides an extremely sensitive and rapid assay for quantifying luciferase expression in genetically altered cells or tissues.

Dual reporters are commonly used to improve experimental accuracy. The term "dual reporter" refers to the simultaneous expression and measurement of two individual reporter enzymes within a single system. In genetic reporting, examples that currently benefit from dual-reporter assays include individual cells or cell populations (such as cells dispersed in culture, segregated tissues, or whole animals) genetically manipulated to simultaneously express two different reporter genes. Most frequently, the activity of one gene reports the impact of the specific experimental conditions, while the activity of the second reporter gene provides an internal control by which all sets of experimental values can be normalized. Normalizing the activity of the experimental reporter to the activity of the internal control minimizes experimental variability caused by differences in cell viability or transfection efficiency. Other sources of variability, such as differences in pipetting volumes, cell lysis efficiency and assay efficiency, can be effectively eliminated. Thus, dual reporter assays often allow more reliable interpretation of the experimental data by reducing extraneous influences.

In genetic reporting, examples that currently benefit from dual-reporter assays include individual cells or cell populations (such as cells dispersed in culture, segregated tissues, or whole animals) genetically manipulated to simultaneously express two different reporter genes. Most frequently, the activity of one gene reports the impact of the specific experimental conditions, while the activity of the second reporter gene provides an internal control by which all sets of experimental values can be normalized.

Cell-free reconstituted systems that may benefit from dual-enzyme reporter technology are cellular lysates derived for the simultaneous translation, or coupled transcription and translation, of independent genetic materials encoding experimental and control reporter enzymes. Immuno-assays may, likewise, be designed for dual-reporting of both experimental and control values from within a single sample.

Currently, genes encoding firefly luciferase (luc), chloramphenicol acetyl transferase (CAT), beta-galactosidase (lacZ), beta-glucuronidase (GUS) and various phosphatases such as secreted alkaline phosphatase (SEAP) and uteroferrin (Uf; an acid phosphatase) have been combined and used as co-reporters of genetic activity. The following references provide representative examples of these various reporter genes used in combined form for the purpose of dual-reporting of genetic activity: luc and GUS: Leckie, F., et al., 1994; luc and CAT, and luc and lacZ: Jain, V. K. and Magrath, I. T., 1992; CAT and lacZ: Flanagan, W. M. et al., 1991; SEAP and Uf: Kondepudi, et al., 1994. See also Promega Dual-Luciferase® Reporter Assay system as well as Promega pGL3 Luciferase Reporter Vectors (available from Promega Corporation, Madison, Wis.) as well as U.S. Pat. Nos. 5,744,320 and 5,670,356 (assignee: Promega Corporation), which are incorporated by reference in their entirety.

When luciferase is combined with a sample for the purpose of detecting a product such as ATP or the occurrence of a biospecific event, e.g., inhibition or activation of caspase or P-450 activity, either in an enzyme assay or single/dual reporter assay format, one or more of the compounds in a chemical library used for high throughput drug screening may adversely interact with luciferase and thus interfere with the assay. For instance, in a caspase assay compounds that only inhibit caspase will result in decreased luminescence and would not be easily distinguishable from compounds that only inhibit luciferase activity which also decreases luminescence. There is a need for luciferase-based assays with improved tolerance for compound interference, especially when employed in high throughput screening procedures.

SUMMARY OF THE INVENTION

The present invention provides methods, compositions and kits for improved luciferase-based assays with enhanced tolerance for interference by one or more compounds, particularly in high throughput screening of compound libraries. The inventive compositions comprise a luciferase and a tolerance enhancing agent that substantially protects luciferase activity from interference by one or more compounds that inhibit or interact with luciferase during screening assays. An optional ATPase inhibitor may be used, particularly if the sample includes cell lysates or enzyme mixtures with ATPase activity. Preferably, the tolerance enhancing agent is a detergent. The improved composition is useful in any assay that employs luciferase as a component of an assay reagent for determining the effect of one or more compounds on purified enzymes, enzyme mixtures, cell lysates or extracts, and/or tissue homogenates in a sample. For instance, the improved compositions may be used in methods for determining the effect of one or more compounds on kinase enzyme activity, protease activity, P-450 enzyme activity, and ATP utilizing or generating enzyme activity contained in a sample.

The invention provides methods for enhancing the tolerance of a luciferase enzyme activity to compound interference in a luciferase based assay. In one embodiment, the methods comprise contacting a luciferase enzyme with a tolerance enhancement agent in an amount sufficient to substantially protect luciferase activity from interference of the compound.

The invention also provides methods of determining the effect of a compound on a non-luminogenic enzyme activity comprising: (a) providing a compound and a luminogenic molecule, wherein the luminogenic molecule is a substrate of the non-luminogenic enzyme and a pro-substrate of a luciferase enzyme; (b) contacting the compound and the non-luminogenic enzyme so as to produce a first reaction mixture; (c) contacting the first reaction mixture with a reagent composition comprising luciferase, the luminogenic molecule, and a tolerance enhancement agent so as to produce a second reaction mixture, wherein said tolerance enhancement agent being present in an amount effective to at least substantially protect the activity of the luciferase from interference from the compound; (d) detecting luminescence in the second reaction mixture; and (e) determining the effect of the compound on the non-luminogenic enzyme activity, if any, result from the interaction of the compound with the enzyme by measuring and comparing the luminescence of the second reaction mixture with a control reaction mixture. In one embodiment of the invention, the steps are conducted sequentially. In another embodiment of the invention, steps (b) and (c) are conducted simultaneously.

In addition, the invention provides methods of determining the effect of a compound on a non-luminogenic enzyme activity comprising: (a) providing a compound and a luminogenic molecule, wherein the luminogenic molecule is a substrate of the non-luminogenic enzyme and a pro-substrate of a luciferase enzyme; (b) contacting the compound, and the non-luminogenic enzyme so as to produce a first reaction mixture; (c) contacting the first reaction mixture with the luminogenic molecule so as to produce a second reaction mixture; (d) contacting the second reaction mixture with a reagent composition comprising luciferase and a tolerance enhancement agent so as to produce a third reaction mixture, wherein said tolerance enhancement agent being present in an amount effective to at least substantially protect the activity of the luciferase from interference from the compound; (e) detecting luminescence in the third reaction mixture; and (f) determining the effect of the compound on the non-luminogenic enzyme activity, if any, result from the interaction of the compound with the enzyme by measuring and comparing the luminescence of the third reaction mixture with a control reaction mixture. In one embodiment of the invention, the steps are conducted sequentially. In another embodiment of the invention, steps (b) and (c), or steps (c) and (d), or steps (b) to (d) are conducted simultaneously.

In addition, the invention provides methods of determining the effect of a compound on a non-luminogenic enzyme activity comprising: (a) providing a compound for testing and a reagent composition comprising a luminogenic molecule, wherein the luminogenic molecule is a substrate of the non-luminogenic enzyme and a pro-substrate of a luciferase enzyme; the non-luminogenic enzyme; luciferase; and a tolerance enhancement agent, wherein said tolerance enhancement agent being present in an amount effective to at least substantially protect the activity of the luciferase from interference from the compound; (b) detecting luminescence in the final reaction mixture; and (c) determining the effect of the compound on the non-luminogenic enzyme activity, if any, result from the interaction of the compound with the enzyme by measuring and comparing the luminescence of the final reaction mixture with a control reaction mixture.

Furthermore, the invention provides methods of determining the effect of a compound on a non-luminogenic enzyme activity comprising: (a) providing a luminogenic molecule and a compound for testing, the luminogenic molecule is a substrate for the non-luminogenic enzyme and a pro-substrate for luciferase; (b) contacting the compound, the luminogenic molecule and a non-luminogenic enzyme so as to produce a first reaction mixture; (c) contacting the first reaction mixture with a reagent composition comprising luciferase, and a tolerance enhancement agent so as to produce a second reaction mixture, wherein said tolerance enhancement agent being present in an amount effective to at least substantially protect the activity of the luciferase from interference from the compound; (d) detecting luminescence in the second reaction mixture; and (e) determining the effect, if any, of the compound on non-luminogenic enzyme activity resulting from the interaction of the compound with the enzyme by measuring and comparing the luminescence of the second reaction mixture with a control reaction mixture. In one embodiment of the invention, the steps are conducted sequentially. In another embodiment of the invention, steps (b) and (c) are conducted simultaneously.

The invention also provides methods of determining the effect of a compound on a non-luminogenic enzyme activity comprising: (a) providing a compound for testing, a substrate for the non-luminogenic enzyme, a non-luminogenic enzyme, and ATP or ADP; (b) contacting the compound, the substrate, ATP or ADP, and a non-luminogenic enzyme so as to produce a first reaction mixture; (c) contacting the first reaction mixture with a reagent composition comprising luciferase, luciferin, and a tolerance enhancement agent so as to produce a second reaction mixture, wherein said tolerance enhancement agent being present in an amount effective to at least substantially protect the activity of the luciferase from interference from the compound; (d) detecting luminescence in the second reaction mixture; and (e) determining the effect, if any, of the compound on non-luminogenic enzyme activity resulting from the interaction of the compound with the enzyme by measuring and comparing the luminescence of the second reaction mixture with a control reaction mixture. In one embodiment of the invention, the steps are conducted sequentially. In another embodiment of the invention, steps (b) and (c) are conducted simultaneously.

The invention further provides methods of determining the effect of a compound on ATP generating enzyme activity in a sample comprising: (a) providing ADP and a compound for testing; (b) contacting the compound, ADP and a sample so as to produce a first reaction mixture; (c) contacting the first reaction mixture with a reagent composition comprising luciferase, luciferin, and a tolerance enhancing agent so as to produce a second reaction mixture, wherein said tolerance enhancement agent being present in an amount effective to at least substantially protect the activity of the luciferase from interference from the compound; (d) detecting luminescence in the second reaction mixture; and (e) determining the effect, if any, of the compound on ATP generating enzyme activity resulting from the interaction of the compound with the ATP generating enzyme by measuring and comparing the luminescence of the second reaction mixture with a control reaction mixture. In one embodiment of the invention, the steps are conducted sequentially. In another embodiment of the invention, steps (b) and (c) are conducted simultaneously.

The invention further provides methods of determining the effect of a compound on ATP generating enzyme activity in a sample comprising: (a) providing a compound for testing, and contacting the compound with a reagent composition comprising ADP, luciferase, luciferin, and a tolerance enhancing agent, wherein said tolerance enhancement agent being present in an amount effective to at least substantially protect the activity of the luciferase from interference from the compound; (b) detecting luminescence in the second reaction mixture; and (c) determining the effect, if any, of the compound on ATP generating enzyme activity resulting from the interaction of the compound with the ATP generating enzyme by measuring and comparing the luminescence of the second reaction mixture with a control reaction mixture.

In a particular embodiment, a tolerance enhancement agent of the invention can comprise a detergent, for example, a cationic, anionic, non-ionic, or zwitterionic detergent. In another embodiment, a tolerance enhancement agent can comprise a non-detergent, for example, polyethylene glycol, polyvinyl pyridine, crown ether, and cyclodextrin. In yet another embodiment, the detergent can comprise Tergitol® detergent polyglycol ether (nonionic)), Brij 35® detergent (polyoxyethylene 23 lauryl ether), Brij 58® detergent (polyoxyethylene 20 cetyl ether ($HO(CH_2CH_2O)_{20}C_{16}H_{33}$)), Triton X-100® detergent (4-(1,1,3,3-tetramethylbutyl)phenyl-polyethylene glycol (t-Oct-$C_6H_4$—$(OCH_2CH_2)_xOH$, x=9-10)), Triton X-305® detergent 4-(1,1,3,3-tetramethylbutyl)phenyl-polyethylene glycol), Triton N101® detergent (polyoxyethylene 9,10 branched nonylphenyl ether), CHAPS® detergent (3-([3-cholamidopropyl]dimethylammonio]-1-propanesulfonate), Chapso® detergent (3-([3-cholamidopropyl]dimethylammonio)-2-hydroxy-1-propanesulfonate), Bigchap® detergent (N,N-bis(3-D-gluconamidopropyl)cholamide), Thesit® detergent (polyethylene glycol 400 dodecyl ether ($HO(CH_2CH_2O)_n$ $(CH_2)_{11}CH_3$)), Pluronic L64® detergent (poly(ethylene glycol)-block-poly(propylene glycol)-block-poly(ethylene glycol)), Rhodasurf 870® detergent (polyethoxylated (20) oleyl alcohol), Chemal LA-9® detergent (polyoxyethylene 9 lauryl alcohol), Sulfonyl 465® detergent (2,4,7,9-tetramethyl-5-decyne-4,7-diol ethoxylate 10), deoxycholate, CTAB, Pierce C08® detergent (C8=Octyl-β-D-glycopyranoside), or Pierce C10® detergent (n-decyl-β-D-maltoside (C10 alkyl side chain).

In another embodiment, the methods of the invention further comprise correlating luminescence with enzyme concentration or activity.

In one embodiment, the enzyme activity is contained in a sample. In one aspect, a sample can be a purified, partially purified or crude enzyme or mixtures of enzymes, a cell lysate, a tissue homogenate, or a subcellular fraction.

In another embodiment, a non-luminogenic enzyme in a method of the invention can be a protease. In one aspect, the protease can be, for example, trypsin, trypsinase, or caspase. In another aspect, the caspase can comprise caspase-3, caspase-7, caspase-8 or caspase-9. In another aspect, the luminogenic substrate can comprise any masked substrate that is a substrate of the protease and a prosubstrate of the luciferase such as an amino-modified aminoluciferin or a carboxyl protected derivative thereof.

In still another embodiment, the non-luminogenic enzyme can be a cytochrome P-450 enzyme, and the luminogenic substrate can be a D-luciferin derivative, and the tolerance enhancement agent can be Tergitol® detergent, for example, Tergitol NP-9® detergent.

In yet another embodiment, the non-luminogenic enzyme can be a kinase and the detergent can be Tergitol®, Thesit®, or CHAPS® detergent.

In another embodiment, the compound and enzyme in a method of the invention can be contacted for a first predetermined time period prior to contact with the substrate and ATP or ADP. In one aspect, the substrate and ATP or ADP are added sequentially or simultaneously.

In yet another embodiment, an ATP generating enzyme can be a kinase or phosphatase and the tolerance enhancement agent comprises Tergitol®, Thesit®, or CHAPS® detergent.

The invention further provides methods of determining the effect of a compound on a kinase enzyme activity in an assay sample not containing living cells, comprising: (a) providing a compound for testing, a kinase substrate, a kinase enzyme, and ATP or ADP; (b) contacting the compound, the substrate, ATP or ADP, and kinase enzyme so as to produce a first reaction mixture; (c) contacting the first reaction mixture with a reagent composition comprising luciferase, luciferin, and a tolerance enhancement agent so as to produce a second reaction mixture, wherein said tolerance enhancement agent being present in an amount effective to substantially protect the activity of the luciferase from interference from the compound; (d) detecting luminescence in the second reaction mixture; and (e) determining the effect of the compound, if any, on kinase enzyme activity by comparing the detected luminescence to the luminescence of a similar reaction mixture not containing the compound, or containing the compound at a different concentration.

In a particular embodiment, the kinase enzyme is a protein kinase.

In one embodiment, the tolerance enhancement agent comprises a Tergitol® detergent (polyglycol ether (nonionic), Thesit® detergent (polyethylene glycol 400 dodecyl ether ($HO(CH_2CH_2O)_n(CH_2)_{11}CH_3$)), or Chaps® detergent (cholamidopropyl)dimethylammonio]-1-propanesulfonate).

In another embodiment, the compound and kinase enzyme are contacted for a first predetermined time period prior to contact with the substrate and ATP or ADP.

In another embodiment, the substrate and ATP or ADP are added sequentially or simultaneously.

In yet another embodiment, the steps are carried out sequentially.

In yet another embodiment, steps (b) and (c) are carried out simultaneously.

The invention also provides kits comprising, for example: (a) a tolerance enhancement agent for substantially protecting luciferase activity from interference from a test compound; (b) optional luciferase enzyme; (c) optional buffer reagents; and (d) directions for using the kit. In one embodiment, a kit of the invention further comprises ATP and magnesium ions. In another embodiment, a kit of the invention further comprises luciferin, a cell lysing agent, and/or an ATP extracting agent.

These and other embodiments of the invention will become apparent in light of the detailed description below.

DETAILED DESCRIPTION OF THE INVENTION

A. Definitions

Figure 1:
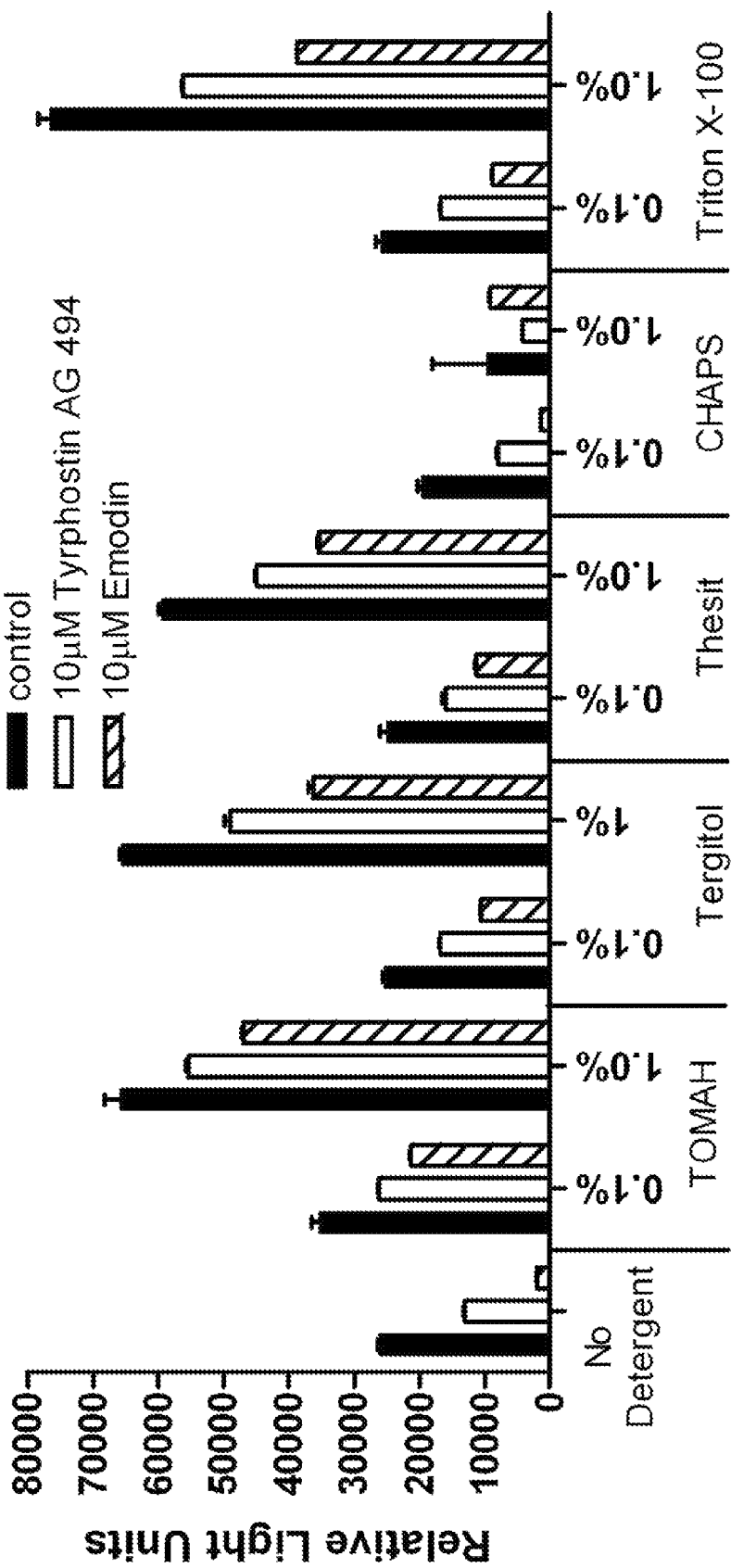
FIG. 1 illustrates the relief of inhibition on luciferase by detergents in a standard luciferase-based reaction in the presence of potential luciferase inhibitors tyrphostin AG494 or emodin. Part (a) compares RLU of control (no detergent) against reaction mixtures that contain 0.1 or 1% of Tomah® detergent (ethoxylated amine), Tergitol® detergent (polyglycol ether (nonionic)), Thesit® detergent (polyethylene glycol 400 dodecyl ether ($HO(CH_2CH_2O)_n(CH_2)_{11}CH_3$)), CHAPS® detergent (cholamidopropyl)dimethylammonio]-1-propanesulfonate), or Triton X-100® detergent (4-(1,1,3,3-tetramethylbutyl)phenyl-polyethylene glycol (t-Oct-$C_6H_4$—$OCH_2CH_2)_xOH$, x=9-10)) as a function of relative light unit values. Part (b) is an analysis that compares the relative % of control against reaction mixtures that contain 0.1 or 1% of Tomah® detergent (ethoxylated amine), Tergitol® detergent (polyglycol ether (nonionic)), Thesit® detergent (polyethylene glycol 400 dodecyl ether (HO(CH$_2$CH$_2$O)$_n$(CH$_2$)$_{11}$CH$_3$)), CHAPS® detergent (cholamidopropyl)dimethylammonio]-1-propanesulfonate), or Triton X-100® detergent (4-(1,1,3,3-tetramethylbutyl)phenyl-polyethylene glycol (t-Oct-C$_6$H$_4$—(OCH$_2$CH$_2$)$_x$OH, x=9-10)).
Figure 1:
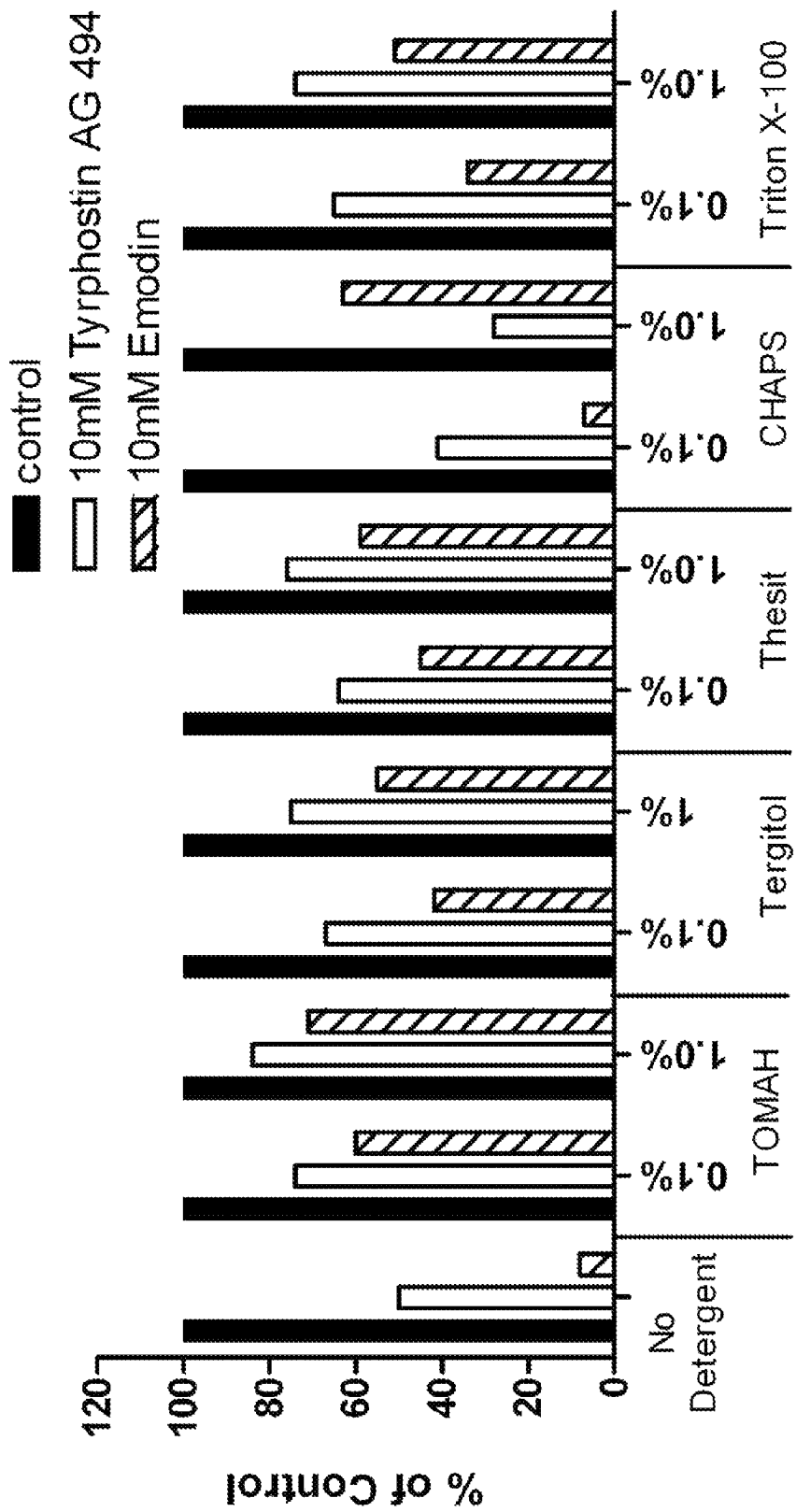
Figure 2:
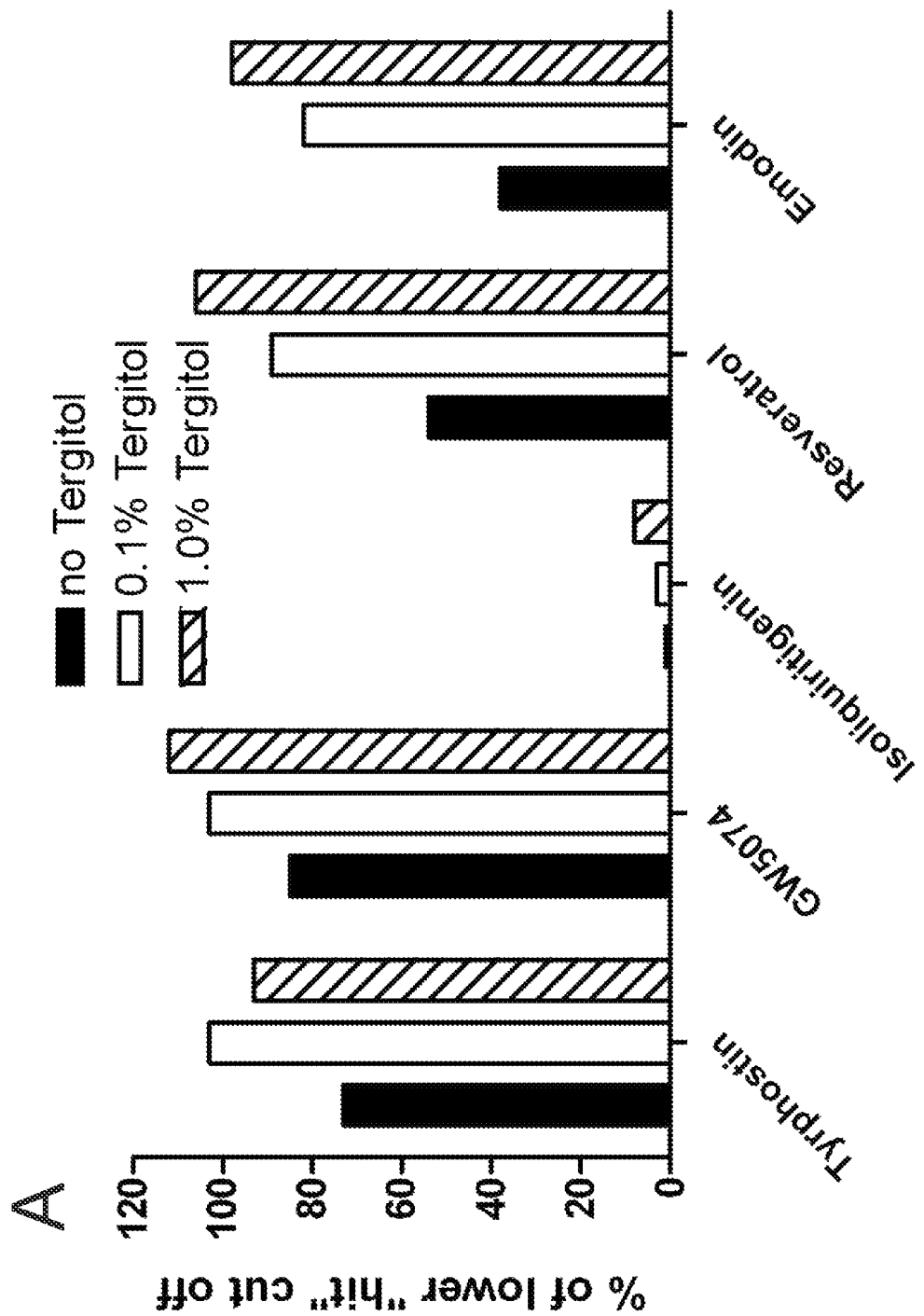
FIG. 2 illustrates the relief of inhibition on luciferase by a detergent, Tergitol® detergent (polyglycol ether (nonionic)), during screening of a known drug library using a standard luciferase-based reaction. Part (a) compares the RLU of control (no detergent) against reaction mixtures. Five drug compounds of the library where found to inhibit luciferase enzyme in the absence of Tergitol® detergent (polyglycol ether (nonionic)). Part (b) is a repeat of part (a) and compares the RLU in the presence of 0.1% Tergitol® detergent (polyglycol ether (nonionic)). Part (c) is a repeat of part (a) and compares the RLU in the presence of 1% Tergitol® detergent (polyglycol ether (nonionic)). Part (d) is a bar graph that shows the dramatic effect of Tergitol® detergent (polyglycol ether (nonionic)) against four of the five drug inhibitors.
Figure 2:
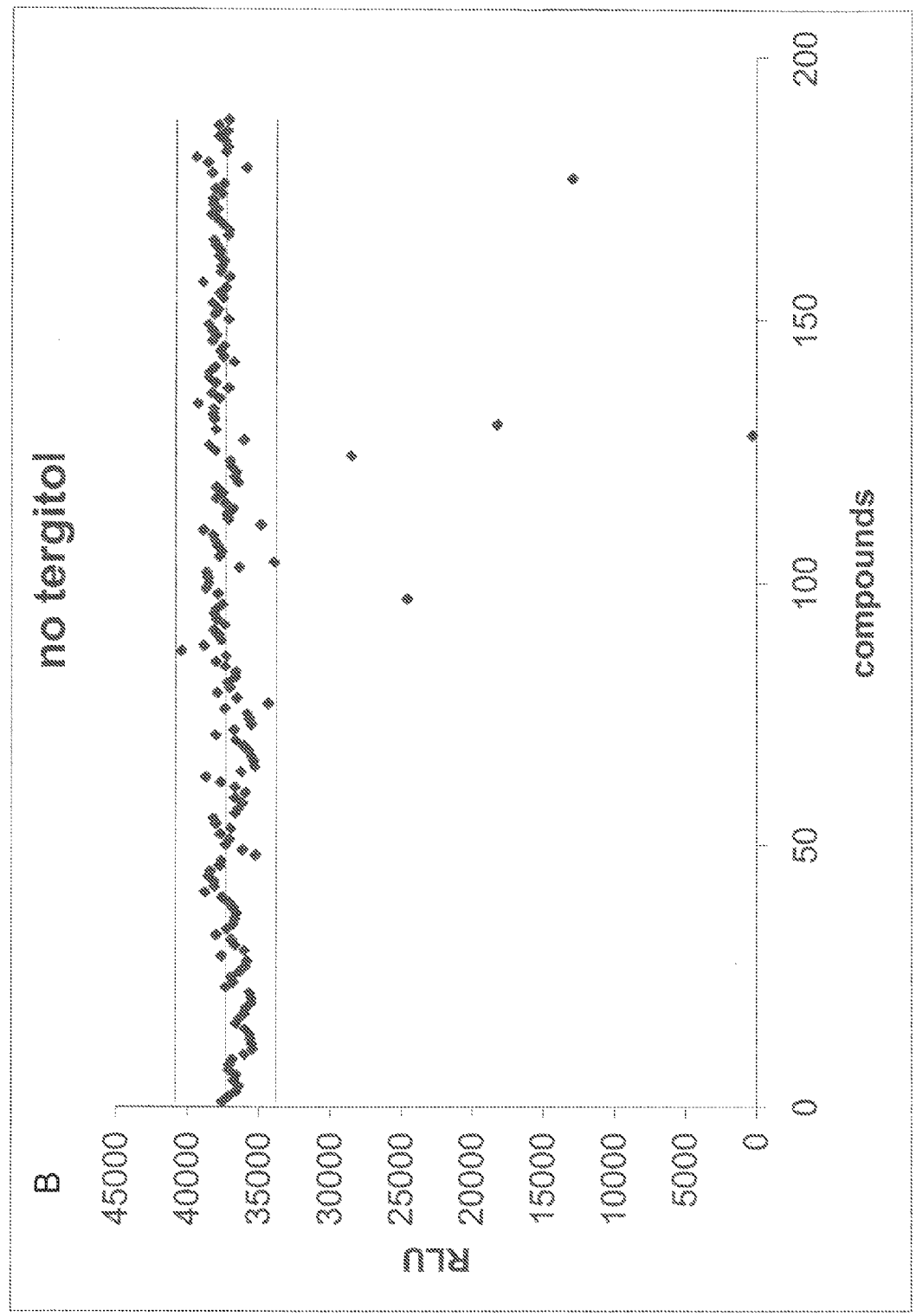
Figure 2:
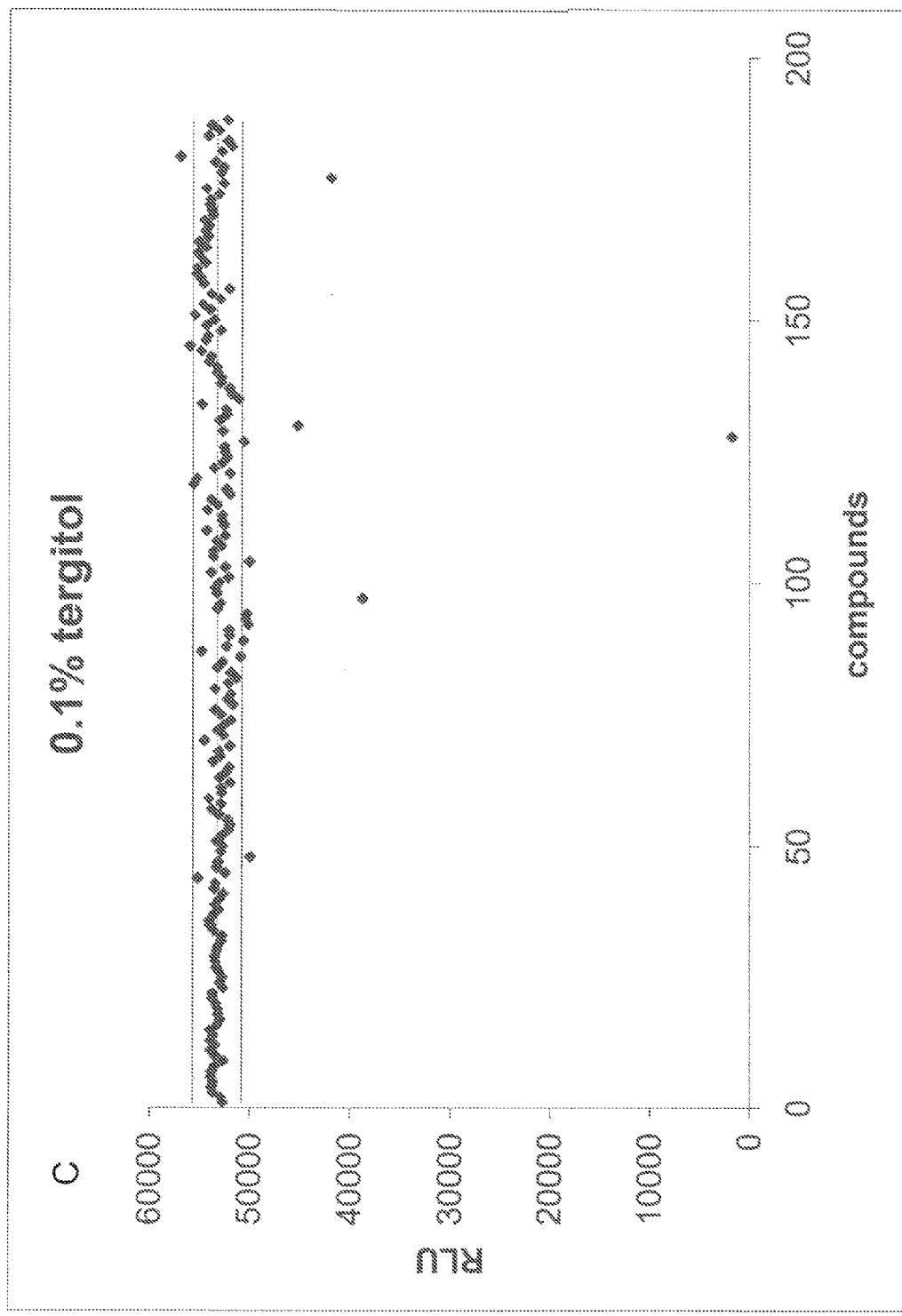
Figure 2:
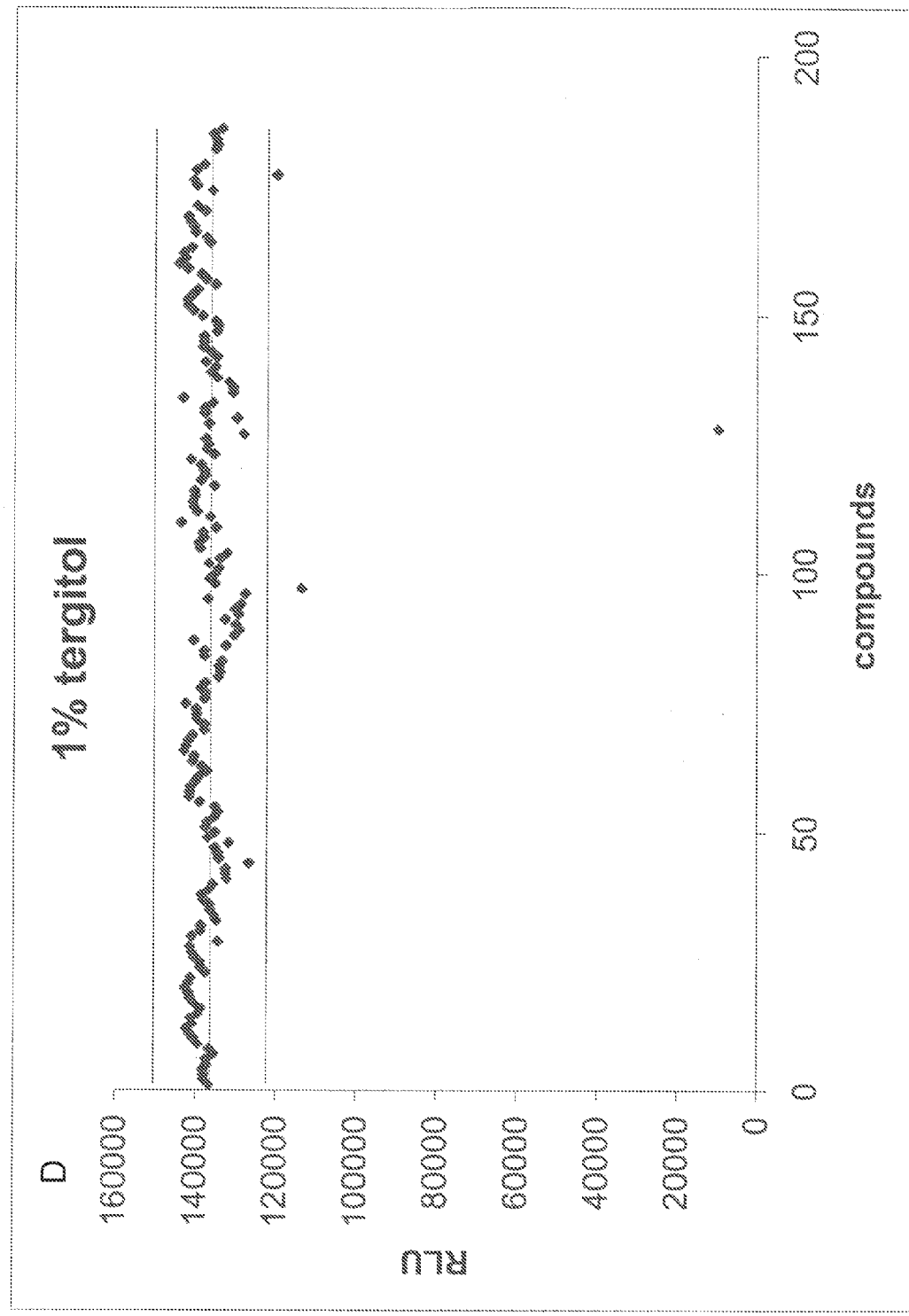

Unless defined otherwise, all technical and scientific terms have the same meaning as is commonly understood by one of skill in the art to which this invention belongs. All cited patents and publications are incorporated by reference in their entirety unless otherwise noted.

The nomenclature recommendations of Demerec et al, 1966, where these are relevant to genetics, are adapted herein. To distinguish between genes (and related nucleic acids) and the proteins that they encode, the abbreviations for genes are indicated by italicized (or underlined) text while abbreviations for the proteins start with a capital letter and are not italicized. Thus, luc or LUC refers to the luciferase nucleotide sequence that encodes luciferase polypeptide or Luc.

An "isolated" or "purified" luciferase is one that has been identified and separated and/or recovered from a component of its natural environment.

As used herein, the term "luciferase" refers to one or more oxygenases that catalyze a light emitting reaction. Thus, luciferase refers to an enzyme or photoprotein that catalyzes a reaction that produces bioluminescence. Luciferases of the invention can be recombinant or naturally occurring, or a variant or mutant thereof, such as a variant produced by mutagenesis that has one or more properties, such as thermal stability, that differ from the naturally-occurring protein. Non-limiting examples of naturally occurring luciferases include, luciferases found among marine arthropods, firefly luciferase, click beetle luciferase, and railroad worm luciferase. A non-limiting example of a luciferase photoprotein is the aequorin photoprotein.

The term "sample" as used herein, is used in its broadest sense and includes, without limitation, a pure, partially purified or crude enzyme or mixtures of enzymes, cell lysates, subcellular fractions, or tissue homogenates.

The term "detection," as used herein, refers to quantitatively or qualitatively determining the effect of a test compound on the sample.

"Percent (%) amino acid sequence identity" is defined as the percentage of amino acid residues in one sequence that are identical to, with, or against amino acid residues in a second sequence in the region of overlap when the two sequences are optimally aligned. To determine percent amino acid identity, sequences are locally aligned and if necessary, gaps are introduced to achieve the maximum percent sequence identity; conservative substitutions are not counted when calculating sequence identity. Amino acid sequence alignment procedures to determine percent identity are well known to those of skill in the art. Publicly available computer software such as BLAST software (available from the National Center for Biotechnology Information, Bethesda, Md.) may be used to align peptide sequences. Those skilled in the art can determine appropriate algorithms and parameters for measuring alignment, including any algorithms and parameters needed to achieve optimal alignment of two amino acid sequences.

When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as:

$$\text{\% amino acid sequence identity}=(X/Y)\cdot 100$$

where X is the number of amino acid residues scored as identical matches in the optimal alignment of A and B by the sequence alignment program or algorithm and Y is the total number of amino acid positions aligned.

B. Method, Composition and Kits

In one embodiment of the invention, the present invention provides compositions with properties comprising a luciferase, a tolerance enhancing agent to improve tolerance for compound interference, and/or one or more optional ATPase inhibitors. The tolerance enhancing agent includes one or more substances such as detergents or sequestering agents that improves the tolerance of the luciferase assay against interference by one or more test compounds during a screening procedure. Some of the tolerance enhancing agents, e.g., detergents, may also function an enzyme anti-degradation agent, or as an ATPase inhibitor. In the case where the tolerance enhancing agent does not act as an ATPase inhibitor and ATPase inhibition is desired, especially when samples having cell lysates are used, one or more ATPase inhibitors may be included. The invention further provides methods using these novel compositions to detect products or occurrence of a biospecific event in a sample measured as a single-step or as a multi-step protocol. Preferably the luminescence resulting from the combination of a composition of the invention with a sample has an extended duration, i.e., diminished by less than about 50% relative to the luminescence just after the composition is combined with the sample. The process of the invention significantly reduces the time and effort of luciferase-mediated detection of the effects of compounds on a sample or detection of occurrence of a biospecific event.

In general, the methods comprise adding a composition ("reagent composition") comprising a luciferase (such as exemplified by, but are not limited to SEQ ID NOs:1-4 described below), a tolerance enhancing agent, and/or one or more optional ATPase inhibitors (if the tolerance enhancing agent does not have ATPase inhibitory activity) to a sample and detecting luminescence, wherein the activity of the reagent has enhanced tolerance to luciferase inhibitors (i.e. the reagent composition is capable of protecting the luminescent signal from inhibition by at least 10% over the reagent in the absence of the tolerance enhancing component). Even more preferably, the tolerance enhancing agent would protect the luminescent signal by at least 30%, 50%, 60%, 70%, 80%, 90%, 99% or greater. The reagent composition may be admixed before use by adding a solution comprising one or more optional ATPase inhibitors to a lyophilized luciferase.

As mentioned above, the invention may be practiced in an environment that generates luminescence with extended duration. Loss of stability is defined as irreversible loss of activity. The reagent composition loses stability over time and the amount of activity lost varies depending on the particular luciferase, tolerance enhancing agent, optional ATPase inhibitor and, when present, enzyme stabilizing agent used. In some instances, the tolerance enhancing agent may have enzyme stabilizing ability and thus may be used in place of a separate enzyme stabilizing agent. Preferably the stability of the reagent composition is demonstrable in the temperature range of about 20° C. to about 37° C. Although the methods of the invention may be used with a sample containing any amount of ATP, it is preferable to use a sample containing a non-saturated amount of ATP (i.e., a range where luminescence is linearly proportional to the concentration of ATP) in assays designed to detect ATP levels. For assays where luciferin levels are measured such as in a Cytochrome P-450 or protease assay that employs pro-luciferin derivatives, it is desirable to employ saturating ATP levels since luciferin, not ATP, levels are being measured.

The luminescence generated by a luciferase reaction is typically detected with a luminometer although other detection means maybe used. The presence of light greater than background level indicates the presence of ATP in the sample. The background level of luminescence is typically measured in the same matrix in which the sample exists, but in the absence of the sample. Suitable control reactions are readily designed by one of skill in the art. Preferred luciferases used in the compositions and methods of the invention generate a stable signal, i.e., they yield enhanced duration of luminescence in a luciferase reaction defined as less than 50% loss of luminescence per hour relative to the luminescence at the time the luciferase reaction was initiated. Preferred luciferases of the invention allow for multiple analyses of a sample over time or analysis of many samples over time, one hour after the luciferase is combined with the reagent composition, more preferably two hours and most preferably four hours or more. Optionally, the luciferases used in the compositions and methods of the invention have enhanced thermostability properties.

Quantifying the amount of emitted light also quantifies the amount of ATP in a sample, and thereby light can be used to quantify living cells. Quantitative ATP values are realized, for example, when the quantity of light emitted from a test sample is compared to the quantity of light emitted from a control sample or to a standard curve determined by using known amounts of ATP and the same luciferase, substrate, and reaction conditions (i.e. temperature, pH, etc.). It is understood that quantification involves subtraction of background values. Qualitative ATP values are realized when the luminescence emitted from one sample is compared to the luminescence emitted from another sample without a need to know the absolute amount of ATP present in the samples, e.g., a comparison of samples in the presence or absence of a test compound. Many such experiments can readily be designed by one of ordinary skill in the art Examples of ATPase inhibitors include detergents, preferably detergents with charged groups such as cationic detergents [e g, DTAB (dodecyltrimethylammonium bromide), CTAB (cetylmethylammonium) and BDDABr (benzyldimethyldodecylammonium bromide)], anionic detergents (e.g., SDS and deoxycholate), and zwitterionic detergents (e g, sulfobetaine 3-10)]. To facilitate the method, a substrate for the luciferase, such as luciferin, may be included in the reagent composition. Other embodiments of the reagent composition may further comprise a compound that prevents an increase in ATP levels in the sample over time. Compounds that prevent an increase in ATP levels in the sample include NaF, vanadate and para-nitrophenylphosphate. Still other embodiments of the reagent composition further comprise a buffer and magnesium. One of skill in the art knows that other cations, such as manganese and calcium, may be suitable substitutes for magnesium.

The reaction composition may also comprise an optional enzyme stabilizing agent. The enzyme stabilizing agent can be any compound that stabilizes the luciferase from degradation. Suitable enzyme stabilizing agents include proteins (such as bovine serum albumin or gelatin) or detergents (preferably non-ionic detergents, most preferably THESIT® detergent (Polyethylene glycol 400 dodecyl ether (HO$(CH_2CH_2O)_n(CH_2)_{11}CH_3)$).

Further, the present invention is useful for determining the effect of small molecules (including organic and inorganic molecules and synthetic and naturally occurring molecules) on cell free enzyme assays, which in turn allows the assessment of whether the small molecule may function as a pharmaceutical. The invention is directed to methods that determine the effect of a small molecule or compound on a cell-free enzyme. One of skill in the art may develop many other such assays for which the invention is useful.

The invention also assembles the elements of the invention into kits. Such kits are designed to determine the effect of a compound or the occurrence of a biological event within a sample, e.g. determining the effects of compounds on enzymes. Kits can be multifunctional such that more than one purpose can be realized. In one embodiment, a kit comprises lyophilized luciferase in one container, while another container contains reconstitution buffer with one or more tolerance enhancing agents and/or one or more ATPase inhibitors. The tolerance enhancement agents and/or ATPase inhibitors may be selected from the substances and detergents already disclosed, for example, DTAB, BDDABr, SDS, deoxycholate, or sulfobetaine 3-10, or a combination thereof.

The kit may also supply a luciferase substrate, such as luciferin, coelenterazine, or a functional derivatives thereof. The kit may also supply magnesium or other cations such as manganese or calcium. To facilitate the use of control experiments with known concentrations of ATP, such as in embodiments of the kits that are used to quantify ATP in a sample, a container that has ATP may also be supplied in such kits. The kit may also supply a compound that prevents an increase in the amount of ATP in the sample over time (e.g., NaF). The kit may also supply an ATP-ase inhibitor (e.g., TCA, DMSA, CTAB, ethanol, and the like). The kit may also supply a buffer. The kit may also supply an enzyme stabilizing agent, e.g., BSA or gelatin or THESIT® detergent (polyethylene glycol 4000 dodecyl ether (HO$(CH_2CH_2O)_n(CH_2)_{11}CH_3)$).

The kit may contain components which, when combined, generate a reagent composition that (i) maintains at least about 30% (preferably at least about 60%, even more preferably at least 70%, 80%, 90%, 95%, 99%) activity for at least about one hour (preferably at least two hours, more preferably four hours), as detected by luminescence when the reagent composition is combined with a sample, and relative to the reagent composition's activity just after it is assembled (i.e., 0 to 10 minutes after the component comprising luciferase is combined with the component comprising an tolerance enhancing agent and optional ATPase inhibitor) and (ii) reduces at least about 25% or at least about 30%, (preferably at least about 40%, even more preferably at least about 50%, 60%, 70%, 80%, 90%, 95%, 99% or any increment therein) of the ATPase activity that is endogenous to the sample relative to the sample's ATPase activity in the absence of the ATPase inhibitor.

The component comprising an ATPase inhibitor may comprise greater than one ATPase inhibitor wherein they are present in the reagent composition at a concentration such that their combined effect reduces at least about 25% or at least about 30%, (preferably at least about 40%, even more preferably at least about 50%, 60%, 70%, 80%, 90%, 95%, 99% or any increment therein) of the ATPase activity that is endogenous to the sample relative to the sample's ATPase activity in the absence of the ATPase inhibitor and when allow for the reagent composition.

The kit preferably comprises a container comprising a buffered detergent solution, said buffered detergent solution at a pH in the range of about pH 6.0 to about pH 9.0. In one embodiment of the invention, said buffered detergent solution comprising DTAB whose concentration in the reagent composition is in the range of about 0.05% to about 2% (w/v) and optionally comprising NaF whose concentration in the reagent composition is in the range of about 1 mM to about 20 mM and optionally comprising THESIT® detergent (polyethylene glycol 400 dodecyl ether $(HO(CH_2CH_2O)_n(CH_2)_{11}CH_3)$), a tolerance enhancing non-ionic detergent agent, whose concentration in the reagent composition is in the range of about 1% to about 5%. The kit additionally comprises a separate container comprising lyophilized luciferase, preferably a luciferase with the sequence of SEQ ID NOs: 1, 2. 3, or 4, most preferably SEQ ID NOs: 2 or 4. Preferably the luciferase, when combined with the buffered detergent solution creating the reagent composition, is at a concentration of 1 μg/ml or greater, more preferably at a concentration of 80 μg/ml or greater. Preferably, the container comprising lyophilized luciferase further comprises lyophilized luciferin. Optionally, the kit further comprises instructions for use of the kit for the purpose of measuring ATP.

In preferred embodiments, the present invention reduces to a single step the manipulations needed for determining enzyme, e.g., kinase, activity in a sample in the presence of one or more test compounds, prior to luminescence measurement. In the single-step ATP assay of the invention, all of the necessary components of the ATP-dependent enzyme (e.g., luciferase), such as the enzyme, substrates, tolerance enhancer substances and ATPase inhibitors are comprised within a reagent composition and are added to a sample at once. In some embodiments, a component of the reagent composition is an enzyme stabilizing agent.

In another embodiment of the invention, methods, compositions and kits are provided for determining the effect of one or more compounds, preferably in a high-throughput screening format, on enzyme, e.g., protease, activity by detecting and quantifying luciferin levels in a sample. The method comprises adding to a sample a composition ("reagent composition") comprising a luciferase enzyme, a tolerance enhancing agent to improve tolerance for compound interference, and a substrate for the protease that is a prosubstrate for the luciferase such as an amino-modified aminoluciferin or carboxyl protected derivative thereof, and detecting luminescence produced in the sample by the conversion of a substrate-derived aminoluciferin into a luminescing compound by luciferase. These masked luciferase substrates are cleaved and unmasked by the protease. For instance, the amino-modified aminoluciferin or derivative thereof has a covalent linkage of a protease substrate to the amino group of aminoluciferin and the protease is capable of cleaving its substrate at the covalent linkage or peptide bond, releasing aminoluciferin, a substrate for luciferase. U.S. patent application No. 60/353,158, filed Feb. 1, 2002 entitled "Bioluminescence protease assay" (assignee: Promega Corp.), incorporated herein in its entirety, describes luciferase-based assays for determining protease activity and useful protease substrates.

In one aspect of this invention, a sensitive luminescent method is provided to determine protease activity, e.g., a caspase, trypsin or tryptase, in the presence of one or more compounds. For instance, the invention provides a luminescent assay method to determine the activity of one or more caspases in the presence of one or more compounds. The method comprises contacting a sample suspected of having one or more caspases with a mixture comprising beetle luciferase and an amino-modified beetle aminoluciferin or a carboxyl protected derivative thereof, and a tolerance enhancing agent wherein the amino group of aminoluciferin or the derivative thereof is modified so as to covalently link a substrate for the caspase or the carboxyl protected derivative thereof via a peptide bond to aminoluciferin. If the sample comprises a caspase having a recognition site in the substrate, the substrate is cleaved at the peptide bond that links the substrate to aminoluciferin, yielding aminoluciferin, a substrate for the luciferase, in the mixture. Luminescence is then detected. The method further comprises correlating luminescence with protease concentration or activity, i.e., increased luminescence correlates with increased protease concentration or activity. As defined herein, the term "functional equivalent" of a reference substrate is a substrate having one or more amino acid substitutions relative to the sequence of the reference substrate, which functionally equivalent substrate is recognized and cleaved by the same protease at a substantially similar efficiency as the reference substrate. Preferably, the increased protease assay sensitivity with methods employing the luminescent substrates described in U.S. patent application No. 60/353,158, filed Feb. 1, 2002 is at least 2 times, more preferably 3, 4, 5, 6, 7, 8, 9, or 10, or even greater, for instance, at least 15, 20, 25, 30, 40, 50, 100, 200, 500, or 1000 times or more, greater than that of a comparable assay employing a conjugate comprising a fluorophore covalently linked to at least one substrate molecule or a functional equivalent thereof. Thus, the methods of the invention may detect less than 5 uU, or less, e.g., less than 1 uU, 0.5 uU or 0.2 uU of caspase in a sample. As used herein, the limit of detection means 3 standard deviations above background noise ("noise" is 1 standard deviation of background and background is a control without caspase).

Using a substrate for caspase 3 and 7 that was linked to either aminoluciferin or rhodamine-110, it was found that the limit of detection for the aminoluciferin-based substrate was 0.2-0.5 uU of purified caspase while that for the rhodamine-1,0-based substrate was 10 uU. It was also found that the limit of detection of caspase expressing cells with the aminoluciferin-based substrate was 15 cells at 1 hour while the limit of detection for the rhodamine-1,0-based substrate was 150 cells at 1 hour. The methods of the invention may be employed with a sample comprising purified, partially-purified, or crude preparations of enzyme.

The invention also provides a luminescent assay method to detect a protease activity where the protease that specifically cleaves a substrate comprising aspartate. The method comprises contacting a sample having one or more aspartate-specific proteases and including one or more compounds with a mixture comprising luciferase, a tolerance enhancing agent, and an amino-modified aminoluciferin or a carboxyl protected derivative thereof, wherein the amino group of aminoluciferin or the derivative thereof is modified so as to covalently link the substrate via a peptide bond to aminoluciferin or a carboxyl protected derivative thereof. The protease having aspartate as a recognition site will cleave the substrate at the peptide bond that links the substrate comprising aspartate to aminoluciferin, yielding aminoluciferin, a substrate for the luciferase in the mixture. Then luminescence is detected in the sample. Preferred proteases that specifically cleave a substrate comprising aspartate include but are not limited to caspases, e.g., any one of caspases 1-14. Preferred substrates comprise $X_1$-$X_2$-$X_3$-D, wherein $X_1$ is Y, D, L, V, I, A, W, or P; $X_2$ is V or E; and $X_3$ is any amino acid, for instance, a substrate comprising DEVD, WEHD, VDVAD, LEHD, VEID, VEVD, VEHD, IETD, AEVD, LEXD, VEXD, IEHD, or PEHD.

The invention also provides a luminescent assay method to determine trypsin or tryptase activity in the presence of one or more compounds. The method comprises contacting a sample having trypsin or tryptase and one or more test compounds with a mixture comprising luciferase and an amino-modified aminoluciferin or a carboxyl protected derivative thereof, and a tolerance enhancer agent, wherein the amino group of aminoluciferin or the derivative thereof is modified so as to covalently link a substrate for trypsin or tryptase via a peptide bond to aminoluciferin or a carboxyl protected derivative thereof. Luminescence is then detected. Preferably, the luminescent assay is more sensitive than a corresponding assay with a conjugate comprising a fluorophore covalently linked to at least one substrate molecule or a functional equivalent thereof. For trypsin, arginine and lysine are functionally equivalent substrates as trypsin cleaves the peptide bond after those residues with substantially similar efficiencies. The increased assay sensitivity with methods employing the luminescent substrates of the invention for trypsin or tryptase is at least 2 times, more preferably 3, 4, 5, 6, 7, 8, 9, or 10, or even greater, for instance, at least 15, 20, 25, 30, 40, 50 or 100 times or more, greater than that of an assay employing a conjugate comprising a fluorophore covalently linked to at least one substrate molecule or a functional equivalent thereof. Using a substrate for trypsin, it was found that the limit of detection for a lysyl-aminoluciferin substrate was 3.0 pg while that for the arginine$_2$-rhodamine-1,0-based substrate was 12-30 pg. Thus, a trypsin assay that employs an amino-modified aminoluciferin substrate is at least 4 times more sensitive than a corresponding assay with a conjugate comprising rhodamine-110 covalently linked to two functionally equivalent trypsin substrates.

Further provided is a luminescent assay method to determine the activity of a protease that specifically cleaves a substrate comprising arginine or lysine in the presence of one or more test compounds. The method comprises contacting a sample having one or more proteases specific for a substrate comprising arginine or lysine and one or more test compounds with a mixture comprising luciferase, a tolerance enhancing agent, and an amino-modified aminoluciferase or a carboxyl protected derivative thereof covalently linked via a peptide bond to a substrate comprising arginine or lysine and a tolerance enhancer agent. Luminescence in the sample is then detected. Preferably, the assay is more sensitive than a corresponding assay with a conjugate comprising a fluorophore covalently linked to the substrate or a functional equivalent of the substrate. As tryptase is released from activated mast cells in association with inflammatory conditions including allergic reactions such as anaphylactic reactions and allergic rhinitis, and trypsin in stool may be indicative of cystic fibrosis, the methods of the invention is particularly useful for screening test compounds that may be useful for anti-inflammatory therapy.

Kits useful in the methods of the invention are also envisioned. Such kits may comprise the amino-modified aminoluciferins or carboxyl protected derivatives of the invention, and instructions for their use, a luciferase, a tolerance enhancing agent and also optionally a buffer for a luminescence reaction.

In another embodiment of the invention, a method is provided for measuring P-450 activity in the presence of one or more test compounds. A reaction mixture comprising one or more P-450 enzymes and one or more test compounds is prepared and incubated for a predetermined time period. Thereafter, the mixture is contacted with a luminogenic molecule and incubated for a predetermined time period. The cytochrome P-450 metabolizes the luminogenic molecule into a substrate for the bioluminescent enzyme in a first reaction. The reaction mixture is then contacted with luciferase and a tolerance enhancing agent. The bioluminescent enzyme then acts on the substrate in a second light emitting reaction. Cytochrome P-450 activity is indirectly determined by measuring the amount of luminescence that is generated from the assay mixture relative to a control mixture. Controls may involve replacement of P-450 enzyme with water or the P-450 buffer, replacement of recombinant P-450 membrane preparation with a similar preparation that lacks P-450 enzyme, elimination of NADPH, or heat denaturation of P-450 enzyme prior to addition of the luciferin substrate. Luminescence can be measured after a predetermined incubation time period or continuously from the time the reaction is initiated. U.S. patent application Ser. No. 10/665,314, filed Sep. 19, 2003, entitled "Luminescence-based methods and probes for measuring cytochrome P-450 activity" (assignee: Promega Corp.), incorporated herein in its entirety, and U.S. patent application Ser. No. 10/665,314, filed Sep. 19, 2003, the disclosure which is hereby incorporated by reference in its entirety, describe luciferase-based assays for determining P-450 activity and useful luminogenic substrates.

P450 activity can be determined using luminogenic molecules that are P450 substrates or a P450 substrate/bioluminescent enzyme pro-substrate, such as, a beetle luciferin or a luciferin derivative. The term "luciferin derivative" as used herein refers to a type of luminogenic molecule or compound having a substantial structure of D-luciferin and maybe a substrate of one or more cytochrome P450 enzymes and a pro-substrate of luciferase. In the presence of cytochrome P450, the compound is metabolized into luciferin, a substrate of luciferase. In the absence of prior P450 metabolism, some of the compound(s) may bind to luciferase as evidenced by their capacity to inhibit a reaction with luciferin, however, they are not turned over as substrate in light-generating reactions. Without being bound by any theory of operation, it is believed that these compounds are most likely competitive inhibitors of luciferase. Useful, but non-limiting, D-luciferin derivatives are disclosed in U.S. patent application Ser. No. 10/665,314, filed Sep. 19, 2003, the disclosure which is hereby incorporated by reference in its entirety.

In another embodiment of the invention, a method is provided for measuring the activity of a cytochrome P450 enzyme. A luminogenic molecule that is a P450 substrate and a bioluminescent enzyme pro-substrate can be contacted with one or more cytochrome P450 enzymes and bioluminescent enzyme, either simultaneously or in a stepwise manner, for a predetermined time. In the presence of P450, the luminogenic molecule is metabolized into a substrate for the bioluminescent enzyme in a first reaction. The bioluminescent enzyme then acts on the substrate in a second light emitting reaction. Cytochrome P450 activity can be determined by measuring the amount of luminescence that is generated from reaction mixture relative to a control (e.g., no P450 enzyme). For the P450 reaction to occur, P450 reductase, NADPH and $Mg^{+2}$ are generally present in the system. Similarly, the presence of ATP and $Mg^{+2}$ is generally necessary for firefly luciferase activity but not for *Renilla* luciferase activity. Any suitable concentration of luminogenic molecule may be employed in the reaction mixture. In practicing this invention, the concentration of the luminogenic molecule generally ranges between about 10 nM to 1 mM, preferably in the linear range of the substrate dose response by a particular P450 isoform, most preferably at the Km for the particular substrate/P450 isoform reaction or at Vmax for that reaction.

P450 activity can also be determined using luminogenic molecules that are natural coelenterazine and coelenterazine derivatives (collectively referred to as coelenterazines). Coelenterazines are known to luminesce when acted upon by a wide variety of bioluminescent proteins, specifically marine luciferases. Examples of marine luciferases include *Renilla* luciferase, aequorin, *Gaussia* luciferase, *Oplophorus* luciferase, and *Cypridina* luciferase. Useful, but non-limiting, coelenterazines are disclosed in U.S. patent application Ser. No. 10/053,482, filed Nov. 2, 2001, the disclosure which is hereby incorporated by reference in its entirety. Coelenterazines are available from Promega Corporation, Madison, Wis. and from Molecular Probes, Inc., Eugene, Oreg. Coelenterazines may also be synthesized as described for example in Shimomura et al., *Biochem. J.* 261: 913-20, 1989; Inouye et al., *Biochem. Biophys. Res. Comm.* 233: 349-53, 1997; and Teranishi et al., *Anal. Biochem.* 249: 37-43, 1997.

The P450 acts on these coelenterazines in one of two ways. In one reaction pathway, the luminogenic molecules are P450 substrates and bioluminescent enzyme pro-substrates and do not exhibit the characteristic coelenterazine chemiluminescent (luminescence in the absence of a bioluminescent enzyme, e.g. *Renilla*-type luciferase). P450 metabolism of the luminogenic molecule in a first reaction generates the substrate for the *Renilla* luciferase. The *Renilla* luciferase then acts on the substrate in a second light-emitting reaction. P450 activity is then ascertained by measuring the luminescence of the reaction mixture relative to a control reaction mixture. In the second reaction pathway, coelenterazine or coelenterazine derivatives exhibit chemiluminescence and are substrates for *Renilla*-type luciferase. P450 metabolism of such a luminogenic molecule results in the loss of chemiluminescence and activity with *Renilla*-type luciferase. In both types of reaction pathways, P450 activity may be detected either directly by a change in chemiluminescence by the action of the P450 alone or indirectly by a change in bioluminescence from a *Renilla*-type luciferase. Useful, but non-limiting, coelenterazines are disclosed in U.S. patent application Ser. No. 10/053,482, filed Nov. 2, 2001, the disclosure which is hereby incorporated by reference in its entirety as well as in U.S. patent application Ser. No. 10/665, 314, filed Sep. 19, 2003, the disclosure which is hereby incorporated by reference in its entirety.

In another aspect of this invention, a method for determining P-450 activity in the presence of one or more test compounds is provided. According to this method, a reaction mixture comprising one or more P-450 enzymes, one or more test compounds, and a luminogenic molecule is prepared and incubated for a predetermined time period. The reaction mixture is then incubated for a predetermined time period. The P-450 enzyme metabolizes the luminogenic molecule and converts it into a substrate for the bioluminescent enzyme. Thereafter, the second reaction mixture is contacted with a luciferase and a tolerance enhancing agent for a predetermined time period. The luciferase enzyme acts on the substrate in a second light emitting reaction. Cytochrome P-450 activity is then indirectly determined by measuring the amount of luminescence that is generated from the reaction mixture relative to a control (e.g., no P-450 enzyme). The tolerance enhancing component permits more accurate quantitation of the Cytochrome P-450 activity if the test compound interacts directly with the luciferase instead of or in addition to the Cytochrome P-450.

In yet another embodiment of the invention, methods, compositions and kits are provided for determining the effect of one or more compounds, preferably in a high-throughput screening format, on an ATP generating enzyme activity. The method comprises adding to a sample including ADP, an ATP generating enzyme, and a compound, a composition ("reagent composition") comprising a luciferase enzyme, a tolerance enhancing agent to improve tolerance for compound interference, and optionally an ATPase inhibitor, and detecting luminescence produced in the sample by the conversion of a substrate (luciferin) into a luminescing compound by luciferase. Representative of ATP generating enzymes include, without limitation, phosphoglycerate kinase or phosphopyruvate kinase. See U.S. Pat. No. 6,235,480, issued May 22, 2001 (assignee: Promega Corporation), which is incorporated by reference in its entirety, describing a luciferase-based assay for determining ATP generating enzyme activity. The reagent composition of the present invention comprises a tolerance enhancing agent to improve tolerance for compound interference and/or one or more optional ATPase inhibitors, preferably a detergent, and a non-endogenous ATP-dependent enzyme, wherein the composition is capable of maintaining at least about 30% enzymatic activity for at least about one hour, preferably at least about 2 hours, more preferably at least about 4 hours, compared to its activity just after (0 to 10 minutes) the enzyme is combined with the ATPase inhibitor, and wherein the one or more ATPase inhibitors are present in the composition at a concentration sufficient to collectively reduce ATPase activity endogenous to the sample by at least about 25%, more preferably at least about 30%, 40%, 50%, 60%, 70%, 80%, 90%, 95% or 99% or any increment therein relative to the ATPase activity endogenous to the sample in the absence of the ATPase inhibitor. In preferred embodiments of the invention, the non-endogenous ATP-dependent enzymes are luciferases.

In a preferred embodiment, the components of the reagent composition of the invention can be supplied as two parts that are admixed shortly before use: (1) a part comprising luciferase and (2) a part comprising a tolerance enhancing agent for improving luciferase tolerance against interference from one or more compounds and one or more optional ATPase inhibitors. The tolerance enhancing agent may have ATPase inhibition activity and thus may be used in place of a separate ATPase inhibitor. The presence of an ATPase inhibitor is desirable with cell lysate samples. The luciferase component may further comprise luciferin and preferably is lyophilized. The luciferase component optionally comprises excipients for lyophilization, protein (luciferase) stabilizer, magnesium (or alternative cation), and a magnesium chelator (or alternative cation chelator). The ATPase inhibitor component may further comprise a buffer, divalent cation metal chelators, magnesium (or alternative cation), a defoaming agent, anti-ATP-generating enzyme agents (e.g., NaF), an enzyme stabilizer (e.g., THESIT® detergent (polyethylene glycol 400 dodecyl ether $(HO(CH_2CH_2O)_n(CH_2)_{11}CH_3)$) and an agent for while in the presence of an ATPase inhibitor (and, optionally, kinase inhibitors) that stabilizes the amount of ATP present in the sample results in a reliable and efficient method for detecting and quantifying cellular ATP for extended periods of time.

C. Luciferases

Luciferase enzymes, whose catalytic products include light, offer high sensitivity, a detectable product and enable easy measurement of ATP or other molecule such as luciferin or luciferin derivative. However, any luminescence-producing enzyme may be used in the methods and compositions of the present invention.

At their most basic level, luciferases are defined by their ability to produce luminescence. More specifically, a luciferase is an enzyme that catalyzes the oxidation of a substrate, luciferin, thereby producing oxyluciferin and photons.

To date, five classes of luciferases have been identified (Jones et al., 1999; Thomson et al., 1997). Of these, beetle luciferases, such as that of the common firefly (family Lampyridae), form a distinct class with unique evolutionary origins (McElroy et al., 1969; White et al., 1969; White et al., 1975). Beetle luciferases are often referred to as firefly luciferases in the literature; however, firefly luciferases are actually a subgroup of the beetle luciferase class. Beetle luciferases may be purified from the lanterns of the beetles themselves or from protein expression systems well known in the art (Baldwin and Green, 2000; Beny and Dolivo, 1976, Branchini et al 1980; Filippova et al., 1989).

Beetle luciferases, particularly firefly luciferase from the North American firefly *Photinus pyralis*, are well known in the art. The *P. pyralis* luciferase (LucPpy) consists of approximately 550 amino acids of 61 kDa as calculated by the protein encoded by the nucleotide sequence of the gene. Another example of a firefly luciferase is *Photuris pennsylvanica* firefly luciferase (LucPpe2; 545 amino acid residues, GenBank 2190534, (Ye et al., 1997)). Mutant luciferases derived from LucPpe2 (e.g., LucPpe2 m78 (also known as 78-OB1O), SEQ ID NO: 1; LucPpe2 m90 (also known as 90-1B5), SEQ ID NO: 2, LucPpe2 m133 (also known as 133-1B2), SEQ ID NO: 3, LucPpe2 m146 (also known as 146-1H2), SEQ ID NO: 4 can be used in methods of the invention. In addition, any luciferase that meets the limitations set forth herein may be used in the composition, method and kits of the invention. The method of making LucPpe2 m78, LucPpe2 m90, LucPpe2 m133, and LucPpe2 m146 is disclosed in PCT/US99/30925.

In certain embodiments, isolated and/or purified luciferases can be used in the present invention. Contaminant components of its natural environment are materials that would typically interfere with diagnostic or therapeutic uses for the luciferase, and may include enzymes, hormones, and other proteinaceous or non-proteinaceous materials. One technique to ascertain purity is applying SDS-PAGE analysis under non-reducing or reducing conditions using Coomassie blue or silver stain. Isolated luciferase includes luciferase in situ within recombinant cells, since at least one component of the luciferase natural environment will not be present. Luciferases can be isolated from biological specimens that produce luciferase or from a cell that expresses an exogenous polynucleotide encoding a desired luciferase (e.g., a nucleotide encoding 78-OB10, 90-1B5, 133-1B2, or 146-1H2 (SEQ ID NOs: 5-8, respectively)). Such techniques are well known to those of skill in the art.

The naturally-occurring substrate for beetle luciferases is firefly luciferin, a polyheterocyclic organic acid, D-(−)-2-(6'-hydroxy-2'-benzothiazolyl)-$\Delta^2$-thiazolin-4-carboxylic acid (luciferin). Luciferin may be isolated from nature (e.g. from fireflies) or synthesized. Synthetic luciferin can have the same structure as the naturally occurring luciferin or can be derivatized, so long as it functions analogously (Bowie et al., 1973, Branchini, 2000; Craig et al., 1991; Miska and Geiger, 1987; Yang and Thomnason, 1993). Examples of derivatives of luciferin include D-luciferin methyl ester, D-luciferyl-L-phenylalanine, D-luciferyl-L-N arginine, D-luciferin-O sulphate and D-luciferin-O-phosphate (Miska and Geiger, 1987), esters of luciferases that are hydrolyzed or acted upon by esterases to luciferin by components in a sample (Craig et al., 1991; Yang and Thomason, 1993). Other examples of useful luciferin analogs include naphthyl- and quinolylluciferin, which emit light in the green and red light spectra respectively (Branchini et al., 1989). There are multiple commercial sources for luciferin (e.g., Promega Corp. Madison, Wis., Molecular Probes, Eugene, Oreg.).

The beetle luciferase-catalyzed reaction that yields luminescence (the luciferase-luciferin reaction) involves firefly luciferin, adenosine triphosphate (ATP), magnesium, and molecular oxygen. In the initial reaction, the firefly luciferin and ATP react to form luciferyl adenylate with the elimination of inorganic pyrophosphate. The luciferyl adenylate remains tightly bound to the catalytic site of luciferase. When this form of the enzyme is exposed to molecular oxygen, the enzyme-bound luciferyl adenylate is oxidized to yield oxyluciferin in an electronically excited state. The excited oxidized luciferin emits light on returning to the ground state.

It is contemplated that the ATP function of the reaction can be performed by an ATP analogue (e.g., dATP). It is also contemplated that other ions can serve as substitutes for magnesium ions (e.g., $Mn^{2+}$ or $Ca^{2+}$). Additionally, oxygen is a reactant of the reaction. Therefore, the reaction should not be conducted under anaerobic conditions. However, it is not generally necessary in practicing the invention to provide oxygen over and above that present in the air. Reactions can take place in closed vessels, provided there is sufficient oxygen in the reaction solution.

Most luciferase-luciferin reactions generate a flash of light that is short lived. However, some of the luciferases that can be used in methods of the invention, e.g., LucPpe2 m146 and LucPpe2 m90 luciferases, under the conditions of the invention generate a "glow-type" luminescent signal with less than 50% loss of luminescence per hour after the reagent composition is combined with the sample.

Any luciferase, luciferase variant, luciferase fragment, or variant luciferase fragment that retains the ability to generate luminescence when used in the reagent composition of the present invention and does not prevent the reagent composition from meeting the stability requirements of the present invention, can be used in the present invention.

A full length luciferase variant will have at least about 80% amino acid sequence identity, preferably at least about 81% amino acid sequence identity, more preferably at least about 82%, 83%, 84%, 85%, 86%, 87%, 88%, 89%, 90%, 91%, 92%, 93%, 94%, 95%, 96%, 97%, 98% amino acid sequence identity and most preferably at least about 99% amino acid sequence identity with a full-length native sequence luciferase sequence and retain the ability to generate luminescence. Ordinarily, variant luciferase fragments are at least about 50 amino acids in length, often at least about 60 amino acids in length, more often at least about 70, 80. 90, 100, 150, 200, 300, 400, 500 or 550 amino acids in length, or more and retain the ability to generate luminescence. A luciferase, luciferase fragment, luciferase variant or variant luciferase fragment may be fused to other non-luciferase amino acid sequences and still be functional in the invention.

Full length luciferase, fragments of luciferase, variants of luciferase, and variant fragments of luciferase enzyme used in the compositions and methods of the present invention may be purified from a native source or prepared by a number of techniques, including (1) chemical synthesis, (2) enzymatic (protease) digestion of luciferase, and (3) recombinant DNA methods. Chemical synthesis methods are well known in the art, as are methods that employ proteases to cleave specific sites. To produce segments of luciferase protein segments of luciferase or luciferase variants can be made and then expressed in a host organism, such as *E. coli*. Methods such as endonuclease digestion or polymerase chain reaction (PCR) allow one of skill in the art to generate an unlimited supply of well-defined fragments. Preferably, luciferase fragments share at least one biological activity with native luciferase, as well as catalytic activity, although the level of activity may vary from that of the native luciferase.

Any type of amino acid substitution, insertion or deletion, or combination thereof may be used to generate a variant luciferase. However, a luciferase with a conservative amino acid substitution is more likely to retain activity. Useful conservative substitutions are shown in Table A "Preferred substitutions." Conservative substitutions whereby an amino acid of one class is replaced with another amino acid of the same type fall within the scope of the invention if the substitution does not impair luciferase activity.

TABLE A

Preferred substitutions

| Original residue | Exemplary substitutions | Preferred substitution |
| --- | --- | --- |
| Ala (A) | Val, Leu, Ile | Val |
| Arg (R) | Lys, Gin, Asn | Lys |
| Asn (N) | Gln, His, Lys, Arg | Gin |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser(S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge or (3) hydrophobicity, or (4) the bulk of the side chain of the target site might modify luciferase function. Residues are divided into groups based on common side-chain properties as denoted in Table B. Non-conservative substitutions entail exchanging a member of one of these classes for another class.

TABLE B

| Class | Amino acids |
| --- | --- |
| Hydrophobic | Norleucine, Met, Ala, Val, Ley, Ile |
| neutral hydrophilic | Cys, Ser, Thr |
| Acidic | Asp, Glu |
| Basic | Asn, Gln, His, Lys, Arg |
| disrupt chain conformation | Gly, Pro |
| Aromatic | Trp, Tyr, Phe |

Variant luciferase genes or gene fragments can be made using methods known in the art such as oligonucleotide-mediated (site-directed) mutagenesis, alanine scanning, and PCR mutagenesis. Site-directed mutagenesis (Carter, 1986; Zoller and Smith, 1987), cassette mutagenesis, restriction selection mutagenesis (Wells et al, 1985) or other know techniques can be performed on the cloned DNA to produce the luciferase variant DNA (Ausubel et al., 1987; Sambrook, 1989).

1. Selected Luciferases

Any luciferase, luciferase fragment, or variants thereof that emits photons upon oxidation of a substrate may be used in the present invention. Other desirable characteristics, such as thermostability, chemostability, and signal stability, are also contemplated. In addition, the luciferase may be fused to another amino acid sequence and still be functional in the present invention. Such enzymes may be synthesized in vitro or isolated from other organisms.

Naturally occurring luciferases can be found, for example, in bacteria, unicellular algae, coelenterates, beetles (other than *P. pennsylvanica*), fishes, and other organisms. Chemically, all luciferases involve exergonic reactions of molecular oxygen with different luciferins, resulting in photon production (Hastings, 1996; Hastings and Wilson, 1976; Wilson and Hastings, 1998, Wood et al., 1989).

The use of a luciferase other than that from beetles requires an appropriate luciferin molecule that upon oxidation generates a chemically and electrically unstable intermediate or a detectable enzymatic product. Other substrates may be used, as well as other ATP-dependent enzymes that produce a detectable enzymatic product. Detectable products include photons, radioactively-labeled products, insoluble or soluble chromogens, or other products that can be detected visually or through the use of devices.

In certain embodiments, luciferases of the invention possess catalytic activity that depends on ATP and emits photons. In other embodiments, luciferases of the invention have enhanced chemostability in the presence of ATPase inhibitors relative to the level of the *P. pyralis* luciferase (LucPpy) chemostability in the same reaction conditions. In some embodiments, luciferases used in the compositions and methods of the invention generate a stable signal, i.e., they yield enhanced duration of luminescence in a luciferase reaction defined as less than 50% loss of luminescence per hour relative to the luminescence at the time the luciferase reaction was initiated. In still other embodiments, luciferases of the invention can allow for multiple analyses of a sample over time or analysis of many samples over time, one hour after the luciferase reaction is initiated, more preferably two hours and most preferably four hours or more. Optionally, the luciferases used in the compositions and methods of the invention have enhanced thermostability properties. An exemplified luciferase is LucPpe2 m146 (SEQ ID NO:4). Additional examples of enzymes useful in the invention include, but are not limited to, LucPpe2 m78 (SEQ ID NO:1), LucPpe2 m90 (SEQ ID NO: 2), and LucPpe2 ml33 (SEQ ID NO:3).

The luciferases LucPpe2 m78 (SEQ ID NO: 1), LucPpe2 m90 (SEQ ID NO:2), LucPpe2m 133 (SEQ ID NO:3) and LucPpe2 m146 (SEQ ID NO:4) were generated from a mutant of *P. pennsylvanica* (T249M). The nucleic acid sequence encoding this protein was subjected to mutagenic methods including recursive mutagenesis followed by screens for thermostability, signal stability, and substrate binding and is fully described by Wood and Hall (WO 9914336, 1999).

2. Chemostable Luciferases

"Chemostable luciferases" as used herein, defines luciferases that retain activity in the presence of compounds or conditions when those compounds or conditions typically inhibit ATPases and disrupt the function of non-chemostable luciferases such as LucPpy. The above identified luciferases LucPpe2 m78 (SEQ ID NO:1), LucPpe2 m90 (SEQ ID NO:2), LucPpe2m 133 (SEQ ID NO:3) and LucPpe2 m146 (SEQ ID NO:4), were found herein to have enhanced chemostability to ATPase inhibitors.

Thus, in certain embodiments, luciferases of the invention include those that maintain at least about 30% (preferably at least about 60%, 70%, 80%, 90%, 95%, 99%) enzymatic activity as measured by luminescence at least one hour (preferably at least two hours, more preferably at least four hours) after contact with an amount of ATPase inhibitor, preferably a detergent, e.g., cationic detergent (preferably DTAB or BDDABr), anionic detergent (preferably deoxycholate or SDS) or zwitterionic detergent (preferably sulfobetaine 3-10) or combination thereof sufficient to collectively reduce ATPase activity endogenous to a sample by at least about 25% (preferably at least about 30%, even more preferably at least about 40%, 50%, 60%. 70%, 80%, 90%, 95%, 99% or any increment therein) relative to the sample's ATPase activity in the absence of the ATPase inhibitor.

The chemostability of an enzyme also may be indicated by the rate of decline of its activity over time. For example, shortly (0 to 10 minutes) after mixing the ATPase inhibitor and the luciferase, thereby creating the reagent composition, at several subsequent time points an aliquot of the reagent composition is added to a sample and relative light unit (rlu) measurements are obtained shortly thereafter. These measurements may be graphed to determine a trend of decline in enzyme activity in the reagent composition over time.

Chemostable luciferases (e.g., Ppe2 m78, Ppe2 m90, Ppe2 m133, and Ppe2 m146) also retain activity in multi-detergent solutions. Specifically, solutions containing 0.01%, preferably 0.05%, 0.1%, 0.2%, 0.3%, 0.4%, 0.5%, 0.6%, 0.7%, 0.8%, 0.9%, most preferably 0.25% CHAPS® detergent (3-([3-Cholamidopropyl]dimethylammonio)-1-propanesulfonate) with at least 0.01%, preferably 0.05%, 0.1%, 0.2%, and most preferably 0.3% or 1.0% BDDABr, taurocholic or taurolithocholic acids, or DTAB, or 0.01%, preferably 0.05%, 0.1%, 0.2%, 0.3%, 0.4%. 0.5%, 0.6%, 0.7%. 0.8%, 0.9%, most preferably 1.0% of taurocholic or taurolithocholic acids with at least 0.01%, preferably 0.05%, 0.1%, 0.2%, and most preferably 0.3% or 1.0% BDDABr, DTAB, or CHAPS® detergent (cholamidopropyl)dimethylammonio]-1-propanesulfonate). Other multi-detergent solutions in which LucPpe2 m78, LucPpe2 m90, LucPpe2 m133 and LucPpe2 m146 retain activity include 0.01%, preferably 0.05%, most preferably 0.1% TRITON X-100® detergent (4-1,1,3,3-tetramethylbutyl)phenyl-polyethylene glycol (t-Oct-$C_6H_4$—$(OCH_2CH_2)_x$OH, x=9-10)) with at least 0.01%, preferably 0.05%, 0.1%, 0.2%, 0.5%, most preferably 1.0% BDDABr, DTAB, or CHAPS® detergent (cholamidopropyl)dimethylammonio]-1-propanesulfonate), or 0.01%, preferably 0.05%, 0.1%, 0.2%, 0.3%, 0.4%, 0.5%, 0.6%, 0.7%, 0.8%, 0.9%, most preferably 1.0% of taurocholic or taurolithocholic acids with at least 0.01%, preferably 0.05%, 0.1%, 0.2% and most preferably 0.3 or 1.0% BDDABr, DTAB, or CHAPS® detergent (cholamidopropyl)dimethylammonio]-1-propanesulfonate); or 0.05%, 1.0%, 2.0%, 4.0%, preferably 2% polyethylene glycol 400 dodecyl ether (THESIT® detergent (polyethylene glycol 400 dodecyl ether ($HO(CH_2CH_2O)_n(CH_2)_{11}CH_3$)), with at least 0.05%, preferably 0.1%, 0.2% and most preferably 0.3% or 1.0% BDDABr, DTAB, or CHAPS® detergent (cholamidopropyl) dimethylammonio]-1-propanesulfonate).

3. Thermostable Luciferase

In some embodiments, a thermostable luciferase that produces luminescence or other thermostable ATP-dependent enzyme that produces a detectable signal can be used in a method of the invention, especially in samples that are treated with heat immediately prior to ATP detection. A thermostable polypeptide remains active at temperatures that inactivate or denature other proteins. The LucPpe2 m78, LucPpe2 m90, LucPpe2 m133 and LucPpe2 m146 enzymes display increased thermostability compared to luciferases found in nature or encoded from polynucleotides isolated from nature.

D. Kits

When the invention is supplied as a kit, the different components of the composition may be packaged in separate containers and admixed prior to use. The different components of the invention may comprise subsets of these parts and may be combined in any way that either facilitates the application of the invention or prolongs storage life.

The following sections are intended to provide certain examples of kit components. One of skill in the art will recognize that the actual components provided in a kit of the invention will vary depending on which particular assay is to be performed.

1. Luciferase-Luciferin Component

All luciferases, luciferase variants, luciferase fragments and variant luciferase fragments that catalyze an ATP-dependent reaction and generate luminescence are contemplated for use in the invention. Some embodiments eliminate the luciferin; for example, allowing a user to supply a luciferin of his/her choice, or the luciferin may be provided separately. The type of luciferin provided may vary but it must be a substrate for the type of luciferase provided.

In one embodiment, a kit supplies the luciferase as an anhydrous preparation. Anhydrous preparations of luciferase may be lyophilized, in which water is removed under vacuum, freeze-dried, crystallized, or any other method that removes water that does not inactivate luciferase. Excipients that bulk the preparation and stabilize luciferase, such as serum albumins or Prionex, may also be included. In other embodiments, luciferase may be suspended in an aqueous composition comprising glycerol or other solvent in which the enzyme is stable. The skilled artisan can easily determine the amounts of the various constituents that work in the compositions and methods of the invention.

2. Tolerance Enhancing Agents

A luminescence assay provides correlation between a biological or biochemical process and light output. Interference by a compound may disrupt or alter correlation to some degree. A "tolerance enhancing agent" of the invention can substantially protect luciferase activity by minimizing the effect of an interfering compound in a luciferase-based assay system by at least about 10%, preferably about 30, 50, 60, 70, 80, 90, 95, 96, 97, 98, 99 and most preferably about 100%, relative to a system without interfering compound and bring the assay closer to correlation. These tolerance enhancing agents include, without limitation, detergents (e.g., cationic, anionic, non-ionic and/or zwitterionic) and non-detergents. Examples of non-detergent tolerance enhancing agents include, without limitation, polyethylene glycol, polyvinyl pyrrolidone, and cyclodextrins. The selection and amount used of a particular tolerance enhancing agent suitable for a particular luciferase-based assay may be determined by a number of ways, including titrating various concentrations of agent in a luciferase-based assay that includes a known luciferase inhibitor and comparing the luminescence obtained from such an assay against a second assay that employs no or reduced amounts of tolerance enhancing agents. Any suitable general luciferase inhibitor may be used as a standard inhibitor agent for identifying and screening tolerance enhancement agents. The example below provides a representative procedure for screening of several tolerance enhancement agents and use of a known general luciferase inhibitor, isoliquirtigenin, as a standard for screening the agents.

In practicing this invention, one or more tolerance enhancing agents may be used in a luciferase-based assay to determine the effect of one or more compounds on enzyme or cellular activity. The amount of tolerance enhancing tolerance enhancing agents that is present in the reagent is such that it is effective to at least substantially protect the activity of the luciferase from interference from one or more compounds in a screening procedure. Any suitable cationic, anionic, zwitterionic, or non-ionic detergent may be used in this invention so long as it functions to enhance luciferase tolerance against one or more compounds in a screening procedure, particularly in high throughput screening procedure. For instance, suitable, but non-limiting, examples of detergents include Tergitol® detergent (nonionic) (polyglycol ether (nonionic)); Brij 35® detergent (polyoxyethylene 23 lauryl ether) (nonionic); Brij 58® detergent (polyoxyethylene 20 cetyl ether ($HO(CH_2CH_2O)_{20}C_{16}H_{33}$)) (nonionic); Triton X-100® detergent (4-(1,1,3,3-tetramethylbutyl)phenyl-polyethylene glycol (t-Oct-$C_6H_4$—$(OCH_2CH_2)_xOH$, x=9-10)) (nonionic); Triton X-305® detergent 4-(1,1,3,3-tetramethylbutyl)phenyl-polyethylene glycol) (nonionic); Triton N101® detergent (polyoxyethylene 9,10 branched nonylphenyl ether) (nonionic); Chaps® detergent (cholamidopropyl)dimethylammonio]-1-propanesulfonate) (zwitterionic); Chapso® detergent (3-([3-cholamidopropyl]dimethylammonio)-2-hydroxy-1-propanesulfonate) (zwitterionic); Bigchap® detergent (N,N-bis(3-D-gluconamidopropyl)cholamide) (nonionic); Thesit® detergent (polyethylene glycol 400 dodecyl ether ($HO(CH_2CH_2O)_n(CH_2)_{11}CH_3$)) (nonionic); Pluronic L64® detergent (poly(ethylene glycol)-block-poly(propylene glycol)-block-poly(ethylene glycol)) (nonionic); Rhodasurf 870® detergent (polyethoxylated (20) oleyl alcohol); Chemal LA-9® detergent (polyoxyethylene 9 lauryl alcohol); Sulfonyl 465® detergent (2,4,7,9-tetramethyl-5-decyne-4,7-diol ethoxylate 10); Deoxycholate (anionic); and CTAB (cationic); Pierce CO8® detergent (C8=Octyl-β-D-glycopyranoside); Pierce C10® (n-decyl-β-D-maltoside (C10 alkyl side chain); and Tergitol®, e.g., Tergitol NP-9® detergent (nonylphenol polyethylene glycol ether ($C_9H_{19}C_6H$—$(OCH_2CH_2)_9OH$)). For luciferase-based assays for determining enzyme activity in the presence of one or more test compounds, Tergitol® detergent (polyglycol ether (nonionic)) (for P-450 and kinase activity), Thesit® detergent (polyethylene glycol 400 dodecyl ether (HO$(CH_2CH_2O)_n(CH_2)_{11}CH_3$)) (for kinase), CHAPS® detergent (cholamidopropyl)dimethylammonio]-1-propanesulfonate) (for kinase activity) are preferred.

3. ATPase Inhibitor Component

In one embodiment, particularly useful when ATP concentrations of a sample are to be measured, the kit comprises a component containing one or more ATPase inhibitors within a solution optionally containing other functional components, such as buffers, defoamers, enzyme stabilizers, and the like. This component may be supplied as a working solution or as a concentrate. The ATPase inhibitor component (e.g., CTAB) may be packaged separately. The ATPase inhibitor may be any of those described herein above. This component may further comprise agents that chelate metal ions that may interfere with the luciferase-luciferin reaction (e.g. EDTA, EGTA), magnesium (preferably supplied as a salt, such as sulfate or chloride; or other functionally equivalent cation), defoaming agents, and inhibitors of ATP generating enzyme (e.g. NaF). Buffers that maintain pH of the working solution, e.g. citrate or MES (which may be supplied as a salt, such as sodium or free acid or base) or any other appropriate buffer may be used. Instructional materials may also be enclosed in the kit as well as materials that may act as standards or controls, depending on the purpose of the kit.

One aspect of the invention is an ATPase inhibitor, preferably a detergent that inhibits ATPases, more preferably a detergent with a charged group, e.g., cationic detergent (preferably DTAB or BDDABr), anionic detergent (preferably deoxycholate or SDS) or zwitterionic detergent (preferably sulfobetaine3-10). Such inhibitors prevent ATPases endogenous to the sample from processing ATP to adenosine diphosphate (ADP) and adenosine monophosphate (AMP) before the luciferase is allowed to utilize the ATP in the sample for the luciferase-luciferin reaction. ATPase inhibitors may inactivate ATPases directly or indirectly. They may bind to ATPases, either in the active sites, thus preventing substrate binding, or denature ATPases, such as by denaturing detergents, or they may selectively sequester ATPases from their substrates.

One embodiment of the present invention uses cationic detergents such as DTAB or BDDABr detergents that act as ATPase inhibitors. However, other ATPase inhibitors are contemplated, such as other cationic detergents, anionic detergents (e.g., SDS and deoxycholate) and zwitterionic detergents (e.g., sulfobetaine 3-10).

For DTAB or BDDABr the concentration in the reagent composition is preferably in the range of about 0.02% to about 5.0%, more preferably about 0.05%, still more preferably about 0.1%, 0.2%, 0.3%, 0.4%, 0.5%, 0.6%, 0.7%, 0.8%, 0.9%, 1.0%, 1.1%, 1.2%. 1.3%, 1.4% and 1.5% and most preferably to a final concentration of about 1.0% in the reagent composition.

Other non-cationic detergent ATPase inhibitors are contemplated for inclusion in the reagent composition; their requirements are that they, like DTAB, preferably inhibit at least about 25%, more preferably at least about 30%, 40%, 50%, 60%, 70%, 80%, 81%, 82%, 83%, 84%, 85%, 86%, 87%, 88%, 89%, 90%, more preferably at least about 91%, 92%, 93%, 94%, 95%, 96%, 97%, 98%, 99% and most preferably about 100% of endogenous ATPase activity in a sample when present in a reagent composition wherein the reagent composition is capable of maintaining at least 30%, 40%, 50%, 60%, 70%, 80%, 81%, 82%, 83%, 84%, 85%, 86%, 87%, 88%, 89%, 90%, more preferably at least about 91%, 92%, 93%. 94%, 95%, 96%, 97%, 98%, 99% and most preferably about 100% activity, as measured by luminescence after the reagent composition is combined with the sample, for at least one hour, more preferably at least 2 hours compared to the reagent composition's activity just after the luciferase is combined with the ATPase inhibitor. Potentially suitable non-cationic detergents that function as ATPase inhibitors include anionic detergents (preferably SDS and deoxycholate), zwitterionic detergents (preferably sulfobetaine 3-10). The concentration of a particular ATPase inhibitor will vary depending on the inhibitor used, and to some extent, the sample being analyzed. One of skill in the art is familiar with methods to determine the appropriate concentration of an ATPase inhibitor for inclusion in the reagent composition; for example, they may examine luciferin-luciferase derived signals over time, comparing those samples that have varying concentrations of a candidate ATPase inhibitor to those samples containing no known ATPase inhibitors.

It is fully anticipated that the most preferred concentration and even the concentration range functional in the methods of the invention will vary for different detergents. For example, SDS concentrations functional in the methods of the invention are about 0.002%. The functional concentration range for a detergent used in the present invention may readily be determined by one of skill in the art using the methods disclosed herein.

It is contemplated that some ATPase inhibitors, at some of the concentrations useful in the invention, may be insoluble or have low solubility in aqueous solutions. These compounds may first be dissolved in an organic solution (e.g., dimethyl sulfoxide or dimethylformamide) and then diluted into the reagent composition for use in the composition and methods of the invention.

4. Inhibitors of ATP-Generating Enzymes

In some samples, enzymes such as kinases may be active, allowing for continued production of ATP. Because the ATP concentration is determined at a specific time, if such enzymatic activity is left unchecked, then an over-estimation of the ATP concentration will be made. To counter such ATP-generating activity where an end-point analysis is desired, inhibitors of ATP production can be used. For end-point analysis, inactivation of the kinase reaction can be advantageous because it ensures a more stable luminescent signal. Although the action of a specific inhibitor may be incompletely understood, their usefulness is not obviated. Examples of useful compounds include NaF, which is useful at concentrations of at least 1 mM, preferably 2 mM to 100 mM or any increment therein; 2 mM is most preferred. Any such inhibitor may be used, however, if it does not adversely affect luciferase so as to take it outside the utility of the invention. One of skill in the art will know how to determine the appropriate concentration of such an inhibitor, whether the inhibitor is novel or well-known. Other inhibitors of ATP generating enzymes include, but are not limited to, vanadate, paranitrophenylphosphate and dichloroacetic acid (Kiechle et al., 1980).

5. Buffers

Any buffers that maintain suitable pH for the working solution and do not interfere with the luciferase-luciferin reaction are contemplated. The preferred pH range is between about pH 4.5 and about pH 9.0, more preferably between about pH 6.0 and about pH 8.0. For P-450 activity measurements the luciferase assay is performed at about pH 8.4. In addition to MES and citrate buffers, other buffers, such as phosphate buffered saline (PBS), Tris, N-(2-Hydroxyethyl) piperazine-N'-(2-ethanesulfomc acid) (HEPES), piperazine-I,4-bis(2-ethanesulfonic acid) (PIPES), borate, and any other buffer known to those of skill in the art may be suitable. Selection of appropriate buffers depends on pH buffering capacity and interaction with the luciferase-luciferin reaction.

6. Defoamers

Defoaming agents are desirable to prevent foam from interfering with the detection of bioluminescence, especially in applications that quantify luminescence. Such agents as MAZU® defoaming agent (BASF) may be organic or silicone based. Selection of defoamers depends on their ability to eliminate foam without interfering with the luciferase-luciferin reaction.

7. Cations

Cations may also be included when necessary, for example in the beetle luciferase-luciferin reaction, which is dependent not only on ATP, but also on magnesium ions. To assure luciferase activity in such cases, magnesium may be exogenously supplied. In addition to magnesium sulfate, other salts of magnesium are contemplated, such as magnesium chloride, magnesium gluconate, magnesium acetate, magnesium bromide, magnesium carbonate, etc. In any case, the magnesium complex must dissociate to make $Mg^{2+}$ ions available to the luciferase and not interfere with the luciferase-luciferin reaction. One of skill in the art is aware that other cations may be functional in place of magnesium. These include calcium and manganese.

In some applications, endogenous magnesium should be sufficient, in which cases exogenous magnesium could be eliminated.

8. Stabilizing Agents

While resistant to the action of nonionic and low concentrations of zwitterionic detergents (Simpson and Hammond, 1991), native firefly luciferase is inactivated by cationic detergents, such as benzalkonium chloride, benzethonium chloride, CTAB (cetyltrimethylammonium), DTAB (dodecyltrimethylammonium bromide), and methylbenzethoniumchloride (Simpson and Hammond, 1991). Where enhanced luciferase stability is desirable, a stabilizing agent can be provided in a kit.

The stabilizing agent can be any compound that stabilizes a luciferase from degradation. Suitable stabilizing agents include proteins (such as bovine serum albumin or gelatin) or detergents (preferably non-ionic detergents, most preferably THESIT® detergent (polyethylene glycol 400 dodecyl ether $(HO(CH_2CH_2O)_n(CH_2)_{11}CH_3)$)).

9. Other Agents

Other agents that may be included in a kit include agents that are known to enhance the duration of luminescence resulting from a luciferase reaction, such as Co-enzyme A (Co A), thiol reagents, such as dithiothreitol and β mercaptoethanol (Wood, U.S. Pat. No. 5,283,179, 1994; Wood, U.S. Pat. No. 5,650,289, 1997), metal ion chelators such as EDTA to prolong the signal and protease inhibitors (Schemrer, U.S. Pat. No. 5,618,682, 1997; Scheirer, U.S. Pat. No. 5,866,348, 1999) or high concentrations of salts (Van Lune and Trer Wiel, WO 00/18953, 2000).

10. Other Kit Contents

Kits may also include reagents in separate containers that facilitate the execution of a specific test, such as cell viability, cytotoxicity, cell proliferation, or determination of ATP concentration. For example, ATP may be supplied so that standard curves may be determined or to be used as internal controls. Also, a luciferin may be supplied so that a luciferin standard curve may be determined. The kit may supply a sample-gathering component such as a membrane, filter or swab.

11. Containers or Vessels

The reagents included in the kits can be supplied in containers of any sort such that the life of the different components are preserved, and are not adsorbed or altered by the materials of the container. For example, sealed glass ampules may contain lyophilized luciferase or buffer that have been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar tolerance enhancing agents as ampules, and envelopes, that may consist of foil-lined interiors, such as aluminum or an alloy. Plastic containers with screw tops or glass containers with rubber stoppers may also be used. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

12. Instructional Materials

Kits may also be supplied with instructional materials. Instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an Internet web site specified by the manufacturer or distributor of the kit, or supplied as electronic mail. In a preferred embodiment, the instructions instruct the user to combine the luciferase with the tolerance enhancer before adding the reagent composition to a sample or to combine the tolerance enhancer with the non-luminogenic reaction before adding the luciferase to this reaction.

E. Reagent Composition Activity

To measure luminescence and thereby determine the reagent composition activity, the relative light unit (RLU) value generated by the luciferase reaction at a timepoint of interest after the reagent composition is combined with a sample may be measured. For example, an RLU value may be obtained by measuring the resulting luminescence from a sample with a known concentration of ATP (in the case where kinase activity is being measured) or substrate (in the case where protease or P-450 activity is being measured) combined with the reagent composition just after (0-10 min) the component comprising the tolerance enhancer is added to the component comprising the luciferase thereby creating the reagent composition. This is considered 100% activity (uninhibited) under those conditions. If, after combining a compound known to inhibit luciferase (for example, isoliquirtigenin) with the luciferase reaction, the luminescence decreases in intensity, then the relative protection bestowed by a tolerance enhancing agent is equivalent to the relative proximity of the intensity to the uninhibited luminescence. For example, if isoliquirtigenin inhibits luminescence in a reaction by 200-fold in the absence of a tolerance enhancing agent, but only inhibits the luminescence by 100-fold in the presence of a compound, then that compound is a tolerance enhancing agent and it exerts a relative protection of 50%.

In practicing this invention, a reagent composition is generally combined with a sample for the purpose of detecting a product such as ATP or the occurrence of a biospecific event such as enzyme inhibition or activation. Typically, the reagent composition comprises a luciferase and a tolerance enhancement agent to protect luciferase activity from interference by one or more compounds that may inhibit or interact with the luciferase. Ambient oxygen is typically sufficient. Optional ingredients may be included in the reagent composition, depending on the type of assay being conducted. For assays for detecting and/or quantitating ATP detection, the reagent composition includes an ATP-dependent luciferase, a tolerance enhancement agent, luciferin (in saturating or sub-saturating concentrations), and a divalent cation (preferably Mg+2). Buffer and other suitable ancillary components such as ATPase and/or enzyme stabilizers may be present as well.

For assays based on luciferin detection, ATP-dependent or ATP-independent luciferases are generally used. Thus, in one embodiment of the invention involving a one step assay, the reagent composition includes an ATP-dependent luciferase, a luciferase pro-substrate, a tolerance enhancement agent, ATP (saturating or sub-saturating concentration), and a divalent cation (preferably Mg+2). In an alternative embodiment involving a two step assay, the reagent includes ATP-dependent luciferase, ATP, and divalent cation. The luciferase pro-substrate is kept separate from the reagent and added to the sample prior to addition of the reagent composition. In another embodiment, the reagent composition includes an ATP-independent luciferase and a tolerance enhancement agent, and a luciferase pro-substrate such as coelenterazine or coelenterazine derivative. ATP is not needed with ATP-independent luciferases. In an alternative embodiment involving a two step assay, the reagent includes ATP-independent luciferase, ATP, and divalent cation. The luciferase pro-substrate is kept separate from the reagent and added to the sample prior to addition of the reagent composition. Buffer and other suitable ancillary components such as ATPase inhibitor and/or enzyme stabilizers may be present as well.

F. Detecting and Quantifying the Products of the Luciferase Reaction

A luciferase reaction results in the generation of light ("luminescence"). Users may simply visually inspect sample reactions to ascertain the production of light. However, more sensitive instrumentations allow not only detection of faint signals, but also quantification of the light signal. Also contemplated are reactions in which non-light products are measured, according to the nature of the products. Any assay that results in a luminescent signal may benefit from the present invention. Appropriate instruments and methods for such products will be apparent to the skilled artisan.

In all cases in which light is detected, specialized instruments, such as luminometers, can read the light product of a luciferase-luciferin reaction. Any instrument that can detect light of the wavelengths emitted by the luciferase reaction may be used. Such instruments may read samples singularly, or in high-throughput screens, may read many samples housed in the wells of a microwell plates (6, 24, 48, 96, 384, 1536, and so on, well formats). Clearly, the devices used to measure the emitted light do not limit the invention. Other devices that can be used include scintillation counters (Nguyen et al., 1988) or instruments invented or adapted to be sensitive to luminescence, such as photometers (Picciolo, et al, 1977). Photographic film or X-ray film may also be used to detect luminescence. In addition, a user may visually inspect a sample to qualitatively evaluate luminescence.

G. Uses for Luciferase Reactions

The invention is drawn to methods, compositions and kits that are used to effectively and accurately detect and quantify ATP or luciferin levels The invention comprises the addition of a single composition (reagent composition) that comprises a luciferase, and a tolerance enhancing agent and then detecting luminescence. The addition of a tolerance enhancing agent of the invention can minimize the effect on luciferase of a compound, said compound being tested against a target activity or component (e.g., CYP450, protease, kinase, ATP level) and thereby bring luminescence into closer correlation with the target activity or component level.

1. Detecting Products

The methods, compositions and kits of the invention provide for the simple qualitative or quantitative detection of ATP (or ATP analogue which can function as a luciferase substrate) and enzyme activity, (e.g., kinase, protease, or cytochrome P-450 activity) in a sample and further in the presence of one or more test compounds. In preferred embodiments, a simple qualitative experiment in which luminescence is generated in a sample using the invention, a tolerance enhancing agent will minimize the effect of an interfering compound and bring the luminescence into closer correlation with the biological or biochemical process being examined. Luminescence is generated using a reagent composition comprising luciferase such as LucPpe2 m78, LucPpe2 m90, LucPpe2 m133 or LucPpe2 m146, and possibly one or more ATPase inhibitors. In addition, the reagent composition may further comprise one or more of the following components: luciferin, which may be reconstituted from a lyophilized preparation, (alternatively, an appropriate luciferin-analogue substrate), ATPase inhibitor(s), inhibitor(s) of ATP generating enzymes such as kinases for end-point determinations, divalent cation (e.g. magnesium), enzyme stabilizing agent, and buffer.

A sample may be anything that is suspected of containing a bioactivity, e.g., kinase, protease or P-450 enzyme activity, that may be susceptible to one or more compounds in a high throughput screening procedure. Samples include solutions including one or more enzymes, cell lysates, beverages, swabs wiped on surfaces such as those of animals, plants, or inanimate objects, and the like. Other examples of samples include compositions of a known ATP concentration or lysates of cells from any organism, prokaryotic or eukaryotic. Examples of prokaryotic cells include *E. coli, P. aeruginosa, B. subtilis*, and *S. typhimurium*. Eukaryotic cells may be from plants, animals, fungi, insects, etc., or cultured cells from such organisms. Examples include *A. thaliana* and *Brassica* sp., *Chlamydomonas* sp. and *Volvox* sp. (plants), *H. sapiens* and *Mus* sp. (animals), *Saccharoymyces* sp. (esp. *cerevisae* and *pombe*) and *Neurospora* sp. (fungi), *D. melanogaster* and *C. elegans* (insects), in vitro cultured callus cells from any plant, primary cells cultured in vitro from any organism (such as organ explants from, for example, rodents), mammalian cell lines such as Madin-Darby canine kidney (MDCK) and Chinese hamster ovary (CHO) cells, and insect cell lines such as sf9 cells. These examples are furnished only as examples and are not meant to be limiting.

A cell lysate comprises cellular components that are no longer organized into a recognizable intact cellular architecture. Cell lysates may have soluble and insoluble components, either of which may be removed before using the lysate. Lysates may be prepared by any means, including physical disruption using sonication, a dounce, mortar and pestle, freeze-thaw cycling, or any other device or process that destroys the physical integrity of cells; or lysis by detergents such as zwitterionic and nonionic detergents, or cationic detergents, e.g., DTAB or CTAS. Preferably, the cell lysate is produced in such a way that the integrity of the ATP concentration is preserved at the time the cells are harvested. To accurately detect ATP in a sample, enzymes that would degrade cellular ATP or those that would generate ATP are preferably inhibited. In the absence of such inhibitors, there is a high risk of an inaccurate determination of ATP concentration. Inhibitors such as DTAB inactivate ATPases, while other molecules such as NaF inactivate ATP-generating enzyme activity. It is hypothesized, yet not fully understood, that for those cell types in which NaF is effective (e.g. lymphoid cells), NaF is potentially acting to inhibit (a) kinase(s).

Solutions with one or more enzymes include, without limitation, purified enzymes, unpurified enzymes, semi-purified enzymes, solubilized enzymes, partially solubilized enzymes, or membrane-bound enzymes.

Inhibitors of ATP-generating enzymes, those enzymes that have as a product or by-product ATP, such as the activity of kinases, may be incorporated into the reagent composition or kept in a separate container for subsequent incorporation into the reagent composition use in cases where end-point determination of kinase activity is desired. An example of an effective inhibitor is NaF (Bostick, et al., 1982). Such compositions comprise NaF at concentrations of at least 0.5 mM, preferably at least 1 mM, more preferably at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 mM or any increment therein, 2 mM is most preferred. Other inhibitors of ATP-generating enzymes include other kinase inhibitors, such as vanadate, AMP, DAPP (Bostick, et al., 1982) and dichloroacetic acid (Kiechle et al., 1980).

2. Detecting and Quantifying Kinase Activity

The compositions, methods and kits of the invention permit a user to detect and quantify kinase activity by detecting and quantifying the amount of ATP consumed by the kinase in a sample by quantifying the amount of luminescence. The invention is applied to a sample of interest, and also to samples containing known amounts of ATP (controls). The signal generated from applying, the invention to a sample of unknown ATP concentration is correlated to signals generated either by internal controls (the addition of a known amount of ATP to a sample and measuring the subsequent luminescence) or external standard curves, generated by measuring the luminescence of several samples of known ATP concentrations and plotting them graphically. Such methods are known to skilled artisans. (Moyer and Henderson, 1983; Ronner et al., 1999; Stanley, 1989; Wood et al., 1989).

3. Effects of Compounds

The compositions, methods and kits of the present invention can be applied to measure the effects of compounds, such as inorganics, small molecules, peptides, proteins, polypeptides, carbohydrates, lipids, steroids, pollutants, carcinogens, or drugs on a biospecific event when contacted with a sample (Aiginger et al., 1980; Andreotti et al., 1995; Bradbury et al., 2000; Cree and Andreotti, 1997; Crouch et al., 1993; Kangas et al., 1984). These compounds may be catalogued in compound libraries, or tested singly. Such applications of the invention apply controls in which samples are contacted with control compounds whose effects on ATP metabolism or enzyme function are known. Also preferably, controls include samples in which luciferase and the compound are present together to assure that the compound itself is not directly affecting luciferase activity.

The following examples are intended to illustrate the present invention without limitation.

EXAMPLES

Example 1

Tolerance Enhancing Effect of Detergents on the Inhibition of Luciferase

In this Example, an assay that employs a luciferase reporter was used to evaluate whether known P-450 enzyme inhibitors are also inhibitors of luciferase and whether tolerance enhancing effects of several detergents can be used to shield the luciferase against such potential inhibitors of luciferase. There is some concern that compounds under study for cellular modulation or enzyme modulation would also affect the luciferase reaction in a luciferase based cell or enzyme reporter assay system. If this were true, then one would expect to obtain an increased number of false "hits" for an assay screen for inhibitors, for instance. Two potential luciferase inhibitors, Emodin and tyrphostin AG494, were identified from the "Library of Pharmaceutically Active Compounds" (LOPAC) screen. These two compounds are potential inhibitors of certain cytochrome P450 enzymes. The objective of the current experiment was to determine if Emodin and Tyrphostin AG494 are also inhibitors of the luciferase reaction, and further to determine whether the presence of detergents could alleviate any inhibition on luciferase caused by these compounds. Luciferase activity was assayed in the presence of luciferin, with or without the compounds, and in the absence or presence of five different detergents at two different concentrations.

First, three luciferin-inhibitor 2× mixes were prepared. Each contains 100 mM $KPO_4$, 20 nM luciferin, 0.1 mg/ml SD control cell microsomal membranes (Available from BD Gentest, Bedford, Mass.); these membranes were used to mimic assay conditions of particular interest, a P450 assay, without the presence of the P-450 enzyme as P450s are commonly expressed recombinantly in sf9 cell microsomal membranes), ±10 uM Emodin or 10 uM Tyrphostin AG494. The control mix containing no inhibitor was also prepared.

Second, eleven 2× luciferin detection reagents were reconstituted from a lyophilized cake containing UltraGlo® luciferase (100 micrograms/ml, available from Promega Corp.), ATP (400 micromolar), and excipient (0.4% Prionex® excipient (Pentapharm, Basel, Switzerland)) using a buffer (200 mM tricine, pH 8.4, 20 mM $MgSO_4$). The final 2× reaction mixtures contained one of the following:
1/ No detergent
2/ 0.2% TOMAH® detergent (ethoxylated amine)
3/ 2% TOMAH® detergent (ethoxylated amine)
4/ 0.2% Tergitol NP9® detergent (nonylphenol polyethylene glycol ether ($C_9H_{19}C_6H$—$(OCH_2CH_2)_9OH$))
5/ 2% Tergitol NP9® detergent (nonylphenol polyethylene glycol ether ($C_9H_{19}C_6H$—$(OCH_2CH_2)_9OH$))
6/ 0.2% Thesit® detergent (polyethylene glycol 400 dodecyl ether ($HO(CH_2CH_2O)_n(CH_2)_{11}CH_3$))
7/ 2% Thesit® detergent (polyethylene glycol 400 dodecyl ether ($HO(CH_2CH_2O)_n(CH_2)_{11}CH_3$))
8/ 0.2% CHAPS® detergent (cholamidopropyl)dimethylammonio]-1-propanesulfonate)
9/ 2% CHAPS® detergent (cholamidopropyl)dimethylammonio]-1-propanesulfonate)
10/ 0.2% Triton X-100® detergent (4-(1,1,3,3-tetramethylbutyl)phenyl-polyethylene glycol (t-Oct-$C_6H_4$—$(OCH_2CH_2)_xOH$, x=9-10))
11/ 2% Triton X-100® detergent (4-(1,1,3,3-tetramethylbutyl)phenyl-polyethylene glycol (t-Oct-$C_6H_4$—$(OCH_2CH_2)_xOH$, x=9-10))
The final concentration will be either 0%, 0.1% or 1% detergent. Finally, 50 microliters of each luciferin-inhibitor mix was combined with 50 microliters of each luciferin detection reagent in triplicate on white luminometer 96-well plates, mixed, and read on a BMG Fluostar luminometer (BMG). The results are expressed in both RLU and % control and are illustrated in FIG. 1.

FIG. 1 illustrates the relief of inhibition on luciferase by detergents in a standard luciferase-based reaction in the presence of luciferase inhibitors tryphostin or emodin. Part (a) compares RLU of control (no detergent) against reaction mixtures that contain 0.1 or 1% of Tomah® detergent (ethoxylated amine), Tergitol (NP9)® detergent (nonylphenol polyethylene glycol ether ($C_9H_{19}C_6H$—$(OCH_2CH_2)_9OH$)), Thesit® detergent (polyethylene glycol 400 dodecyl ether ($HO(CH_2CH_2O)_n(CH_2)_{11}CH_3$)), CHAPS® detergent (cholamidopropyl)dimethylammonio]-1-propanesulfonate), or Triton X-100® detergent (4-(1,1,3,3-tetramethylbutyl)phenyl-polyethylene glycol (t-Oct-$C_6H_4$—$(OCH_2CH_2)_xOH$, x=9-10)) as a function of rlu values. Part (b) is an analysis that compares the relative % of control against reaction mixtures that contain 0.1 or 1% of Tomah® detergent (ethoxylated amine), Tergitol® detergent (polyglycol ether (nonionic) surfactant), Thesit® detergent (polyethylene glycol 400 dodecyl ether ($HO(CH_2CH_2O)_n(CH_2)_{11}CH_3$)), CHAPS® detergent (cholamidopropyl)dimethylammonio]-1-propanesulfonate), or Triton X-100® detergent (4-(1,1,3,3-tetramethylbutyl)phenyl-polyethylene glycol (t-Oct-$C_6H_4$—$(OCH_2CH_2)_xOH$, x=9-10)).

Example 2

Minimization of False Hit Occurrence Using Tolerance Enhancement Agents

In this Example, screening of a commercially available library, LOPAC™ library (Library of Pharmaceutically Active Compounds, available from Sigma Corp., St. Louis, Mo., USA) was performed to determine the effect of tolerance enhancing agents in protecting the luciferase reaction in a cell based or cell-free luciferase-based assay against potential inhibition by the drug compounds. The LOPAC™ library contains 640 compounds whose pharmaceutical activities are known. This library is commonly used to validate screening protocols that are under development.

From a LOPAC™ library screen of 640 compounds, 189 compounds were identified as inhibiting luminescence from all of three cytochrome P450 isoforms (CYP1A2, CYP1A1, CYP2C9) by >10% of an untreated control. It was reasoned that these might be luciferase inhibitors. If any one of the three CYP450 reactions were not apparently inhibited, then inhibition of the luciferase detection system could be ruled out. For the 189 compounds, there were three possible interpretations of the result. One, the compounds are true inhibitors of the P450s; two, the compounds are inhibiting the luciferase, meaning they are false hits; three, the compounds are inhibiting CYP450 and luciferase. To distinguish between these possibilities, the compounds were screened in the presence of luciferin, without any P450 enzyme. If a compound continues to score as a hit, then it is inhibiting luciferase.

First, in duplicate wells on 96-well white luminometer plates, 2× luciferin-compound mixtures were prepared in 50 microliter, containing 10 uM of each compound, 40 nM luciferin, and 100 mM $KPO_4$ as described in Example 1. Each plate also contained control wells in duplicate, where no compound was added (vehicle alone).

Second, 2× luciferin detection reagents were prepared for each reaction, in triplicate as described in Example 1. The 2× reagents further contain of the following:
1/ No detergent
2/ 0.2% Tergitol NP9
3/ 2% Tergitol NP9
The final detergent concentration will be 0.1% or 1% detergent.

Finally, 50 microliters of each luciferin-inhibitor mix is combined with 50 microliters of each luciferin detection reagent in duplicate on white luminometer 96-well plates, mixed, let sit at room temperature for 15 minutes, and then read on a BMG Fluostar luminometer.

A compound would be considered a "hit" if it is more or less than average±3× standard deviation (SD) of the control (99% confidence interval). On the accompanying graphs (FIGS. 2(a) to 2(d)) each diamond represents one compound, the middle line represents the average of the control (containing no inhibitor), and the two lines outside the middle line represent average±3×SD of the control.

In the absence of any detergent, five compounds were identified as inhibitors of luciferase. Thus in a screen that also contains an enzyme of interest (such as cytochrome P450), these agent would be identified as "false" hits. However in the presence of 0.1% Tergitol, there are only four false hits. Finally, in the presence of 1% Tergitol, only one hit remains, while the other four either no longer inhibit or barely inhibit luciferase.

The results shown in FIGS. 2(A)-(D) demonstrate that it is advantageous to screen drug libraries in the presence of a tolerance enhancing agent such as a detergent because it helps minimize the number of false hits.

Example 3

Tolerance Enhancing Effect of Detergents and Non-Detergents on the Inhibition of Firefly and *Renilla* Luciferases In this experiment, several tolerance enhancing agents were evaluated for their ability to protect luciferases from a known luciferase inhibitor, isoliquirtigenin (ILT) (100 μM, Sigma Chemical). ILT was added to luciferase reactions and the potential tolerance enhancing agents were evaluated for their ability to protect the luciferase from inhibition.

The basic firefly luciferase reactions contained 20 mM HEPES (Sigma Chemical) at pH 8.0, 6.4 mM Magnesium Sulfate (Fisher Scientific), 20 mM Dithiothreitol (City Chemical), 0.63 mM Coenzyme A (Pharmacia Biochemical), 0.4 mM EDTA (Sigma Chemical), 4.0 μM Luciferin (Promega Biosciences), 0.56 mM ATP (Pharmacia Biochemical), and $1.3 \times 10^{-6}$ mg/ml firefly luciferase (Quanti-Lum® luciferease, Promega Corporation).

The basic *Renilla* luciferase reactions contained 100 mM Potassium Phosphate buffer (Sigma Chemical) at pH 7.4, 500 mM Sodium Chloride (Fisher Scientific), 1.0 mM EDTA (Sigma Chemical), 200 nM Coelenterazine (Promega Biosciences), 0.1% Gelatin (Sigma Chemical) and 0.12 nmol/ml *Renilla* luciferase (ChemiCon Chemicals).

ILT was solubilized at 100 mM in dimethyl sulfoxide (Sigma Chemical). ILT was diluted 1:1000 and the protectors were diluted into the reaction mix before the reaction was initiated by the addition of luciferase.

Reaction volume for each sample was 100 μl. Luminescence was integrated for 0.5 seconds per sample in a Turner Biosystems Veritas® luminometer immediately after luciferase was added to the reactions and the reactions were mixed. All measurements were done in triplicate.

The relative protection provided by each compound is calculated as difference between the luminescence generated in the presence and the absence of the protector divided by the total amount of inhibition as represented by the following equation:

$$(L1-L2)/(L3-L4)$$

wherein L1 represents luminescence with inhibitor and tolerance enhancing agent; L2 represents luminescence with inhibitor and no tolerance enhancing agent; L3 represents luminescence with no inhibitor and no tolerance enhancing agent; and L4 represents luminescence with inhibitor and no tolerance enhancing agent.

The relative protection in the presence of no tolerance enhancing agent, therefore, is 0% and in the absence of an inhibitor is 100%. The reactions used to generate luminescence in the absence of either inhibitor or tolerance enhancing agent still contained the solvent utilized to solubilize the inhibitor with which the reaction was to be compared.

| Protector | Source | Reaction Concentration | Relative Protection Against ILT |
|---|---|---|---|
| Firefly luciferase | | | |
| α-Cyclodextrin (Cyclohexaamylose) | Sigma Chemical | 7 Mm | 61% |
| Sucrose | Sigma Chemical | 0.5% (w:v) | 32% |
| Polyvinyl pyrrolidone | Sigma Chemical | 0.1% w:v | 69% |
| CHAPS ® detergent (cholamidopropyl)-dimethylammonio]-1-propanesulfonate) | Sigma Chemical | 0.02% | 18% |
| CHAPS ® detergent (cholamidopropyl) dimethylammonio]-1-propanesulfonate) | Sigma Chemical | 0.10% | 57% |
| Deoxycholate | Sigma Chemical | 0.02% | 81% |
| Tergitol NP-9 ® detergent (nonylphenol polyethylene glycol ether ($C_9H_{19}C_6H$—($OCH_2CH_2$)$_9OH$)) | Sigma Chemical | 0.02% | 88% |
| CTAB | Sigma Chemical | 0.02% | 100% |
| Renilla luciferase | | | |
| α-Cyclodextrin (Cyclohexaamylose) | Sigma Chemical | 1.4 mM | 60% |
| Sucrose | Sigma Chemical | 0.10% (w:v) | 24% |
| Polyvinyl pyrrolidone | Sigma Chemical | 0.10% w:v | 74% |
| CHAPS ® detergent (cholamidopropyl)-dimethylammonio]-1-propanesulfonate) | Sigma Chemical | 0.10% | 14% |
| CHAPS ® detergent (cholamidopropyl) dimethylammonio]-1-propanesulfonate) | Sigma Chemical | 0.50% | 97% |
| Deoxycholate | Sigma Chemical | 0.10% | 72% |
| Tergitol NP-9 ® detergent (nonylphenol polyethylene glycol ether ($C_9H_{19}C_6H$—($OCH_2CH_2$)$_9OH$)) | Sigma Chemical | 0.10% | 97% |
| CTAB | Sigma Chemical | 0.10% | 95% |

As seen in the data above, compounds that convey protection to the luciferase from the inhibitors can be easily determined. Also, the tolerance enhancing agents are not equally effective and the concentration of the tolerance enhancing agent affects the level of protection achieved.

While the present invention has now been described and exemplified with some specificity, those skilled in the art will appreciate the various modifications, including variations, additions and omissions, that may be made in what has been disclosed herein without departing from the spirit of the invention. Accordingly, it is intended that these modifications also be encompassed by the present invention and that the scope of the present invention be limited solely by the broadest interpretation that lawfully can be accorded the appended claims.

The invention claimed is:

1. A method of determining the effect of a compound on a non-luminogenic enzyme activity in an assay sample not containing living cells, comprising:
   (a) contacting a compound for testing, a non-luminogenic enzyme, wherein the non-luminogenic enzyme utilizes or produces ATP, a substrate for the non-luminogenic enzyme, and a nucleotide selected from ATP and ADP, so as to produce a first reaction mixture;
   (b) contacting the first reaction mixture with a reagent composition comprising luciferase, luciferin, and a tolerance enhancement agent so as to produce a second reaction mixture, wherein the tolerance enhancement agent comprises at least one of a detergent or a non-detergent, and is present in an amount effective to substantially protect the activity of the luciferase from interference from the compound, thereby reducing the likelihood of a false positive resulting from the interfering effect of the compound, wherein the non-detergent comprises polyethylene glycol, polyvinyl pyridine, or crown ether;
   (c) detecting luminescence in the second reaction mixture; and
   (d) determining the effect of the compound, if any, on the non-luminescent enzyme activity by comparing the luminescence of the second reaction mixture to a control reaction mixture.

2. The method according to claim 1 wherein the steps are conducted consecutively.

3. The method according to claim 1 wherein steps (a) and (b) are conducted simultaneously to produce a reaction mixture, wherein luminescence is detected in the reaction mixture.

4. The method according to claim 1 where the tolerance enhancement agent comprises a cationic, anionic, non-ionic or zwitterionic detergent.

5. The method according to claim 4 wherein the detergent comprises nonionic polyglycol ether, polyoxyethylene 23 lauryl ether, polyoxyethylene 20 cetyl ether ($HO(CH_2CH_2O)_{20}C_{16}H_{33}$), 4-(1,1,3,3-tetramethylbutyl)phenyl-polyethylene glycol ($t\text{-}^1)ct\text{-}C_6H_4\text{---}(OCH_2,CH_2)_xOH$, x=9-10), 4-(1,1,3,3-tetramethylbutyl)phenyl-polyethylene glycol, polyoxyethylene 9, branched nonylphenyl ether, 3-([3-cholamido propyl)dimethylammonio]-1-propanesulfonate, 3-([3-cholamido propyl)dimethylammonio)-2-hydroxy-1-propanesulfonate, N,N-bis(3-D-gluconamidopropropyl) cholamide, polyethylene glycol 400 dodecyl ether ($HO(CH_2CH_2O)_6(CH_2)_{11}CH_3$), poly(ethyleneglycol)-block-poly(propylene glycol)-block-poly(ethylene glycol), polyethoxylated (20) oleyl alcohol, polyoxyethylene 9 lauryl alcohol, 2,4,7,9-tetramethyl-5-decyne-4,7-diol ethoxylate 10, deoxycholate, cetyl-trimethyl ammonium bromide (CTAB), C8=Octyl-β-D-glucopyranoside, or n-decyl-β-D-maltoside (C10 alkyl side chain) or dodecyltrimethylammonium bromide (DTAB) detergent.

6. The method according to claim 1 wherein the tolerance enhancement agent comprises a non-detergent.

7. The method according to claim 1 wherein the non-luminogenic enzyme is a kinase.

8. The method according to claim 7 wherein the tolerance enhancement agent is a detergent selected from nonionic polyglycol ether, polyoxyethylene 23 lauryl ether, polyethylene glycol 400 dodecyl ether ($HO(CH_2CH_2O)_6(CH_2)_{11}CH_3$), dodecyltrimethylammonium bromide (DTAB) and 3-([3-cholamido propyl)dimethylammonio)-2-hydroxy-1-propanesulfonate detergent.

9. The method according to claim 1 wherein the reaction composition comprises two or more detergents.

10. A method of determining the effect of a compound on a kinase enzyme activity in an assay sample not containing living cells, comprising:
    (a) contacting a compound for testing, a kinase enzyme, a substrate for the kinase enzyme, and a nucleotide selected from ATP and ADP, so as to produce a first reaction mixture;
    (b) contacting the first reaction mixture with a reagent composition comprising luciferase, luciferin, and a tolerance enhancement agent so as to produce a second reaction mixture, wherein said tolerance enhancement agent comprises at least one of a detergent, polyethylene glycol, polyvinyl pyridine, or crown ether, and is present in an amount effective to substantially protect the activity of the luciferase from interference from the compound, thereby reducing the likelihood of a false positive resulting from the interfering effect of the compound;
    (c) detecting luminescence in the second reaction mixture; and
    (d) determining the effect of the compound, if any, on kinase enzyme activity by comparing the luminescence of the second reaction mixture to a control reaction mixture.

11. The method according to claim 10 wherein the kinase enzyme is a protein kinase.

12. The method according to claim 10 wherein the detergent comprises nonionic polyglycol ether, polyoxyethylene 23 lauryl ether, polyethylene glycol 400 dodecyl ether (HO(CH2CH2O)6(CH2)11CH3), dodecyltrimethylammonium bromide (DTAB) or 3-([3-cholamido propyl)dimethylammonio)-2-hydroxy-1-propanesulfonate.

13. The method according to claim 10 wherein the reaction composition comprises two or more detergents.

14. The method according to claim 10 wherein the steps are carried out sequentially.

15. The method according to claim 10 wherein step (b) and step(c) are carried out simultaneously.

* * * * *

SEQUENCE LISTING

<160> NUMBER OF SEQ ID NOS: 8

<210> SEQ ID NO 1
<211> LENGTH: 544
<212> TYPE: PRT
<213> ORGANISM: Photuris pennsylvanica
<220> FEATURE:
<221> NAME/KEY: MISC_FEATURE
<223> OTHER INFORMATION: Mutant luciferase protein LucPpe2m78

<400> SEQUENCE: 1

Met Ala Asp Lys Asn Ile Leu Tyr Gly Pro Glu Pro Phe Tyr Pro Leu
1               5                   10                  15

Ala Asp Gly Thr Ala Gly Glu Gln Met Phe Asp Ala Leu Ser Arg Tyr
            20                  25                  30

Ala Asp Ile Ser Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Val Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
        115                 120                 125

Lys Asn Thr Phe Gln Lys Val Leu Asn Val Lys Ser Lys Leu Lys Ser
    130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Leu Val Met Phe Ser Ser Gly Thr Thr Gly Val Pro Lys Gly Val Met
        195                 200                 205

Leu Thr His Lys Asn Ile Val Ala Arg Phe Ser Leu Ala Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

```
Lys Gly Asp Ala Arg Pro Gly Ser Thr Gly Lys Ile Val Pro Phe His
            355                 360                 365
Ala Val Lys Val Val Asp Pro Thr Thr Gly Lys Ile Leu Gly Pro Asn
370                 375                 380
Glu Pro Gly Glu Leu Tyr Phe Lys Gly Ala Met Ile Met Lys Gly Tyr
385                 390                 395                 400
Tyr Asn Asn Glu Glu Ala Thr Lys Ala Ile Ile Asp Asn Asp Gly Trp
            405                 410                 415
Leu Arg Ser Gly Asp Ile Ala Tyr Tyr Asp Asn Asp Gly His Phe Tyr
                420                 425                 430
Ile Val Asp Arg Leu Lys Ser Leu Ile Lys Tyr Lys Gly Tyr Gln Val
            435                 440                 445
Ala Pro Ala Glu Ile Glu Gly Ile Leu Leu Gln His Pro Tyr Ile Val
        450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
            485                 490                 495
Val Gln Asp Phe Val Ser Ser Gln Val Ser Thr Ala Lys Trp Leu Arg
                500                 505                 510
Gly Gly Val Lys Phe Leu Asp Glu Ile Pro Lys Gly Ser Thr Gly Lys
            515                 520                 525
Ile Asp Arg Ser Val Leu Arg Gln Met Phe Glu Lys His Thr Asn Gly
        530                 535                 540

<210> SEQ ID NO 2
<211> LENGTH: 544
<212> TYPE: PRT
<213> ORGANISM: Photuris pennsylvanica
<220> FEATURE:
<221> NAME/KEY: MISC_FEATURE
<223> OTHER INFORMATION: Mutant luciferase protein LucPpe2m90

<400> SEQUENCE: 2

Met Ala Asp Lys Asn Ile Leu Tyr Gly Pro Glu Pro Phe Tyr Pro Leu
1               5                   10                  15
Glu Asp Gly Thr Ala Gly Glu Gln Met Phe Asp Ala Leu Ser Arg Tyr
            20                  25                  30
Ala Asp Ile Pro Gly Cys Ile Ala Leu Thr Asn Ala His Thr Lys Glu
        35                  40                  45
Asn Val Leu Tyr Glu Glu Phe Leu Lys Leu Ser Cys Arg Leu Ala Glu
50                  55                  60
Ser Phe Lys Lys Tyr Gly Leu Lys Gln Asn Asp Thr Ile Ala Val Cys
65                  70                  75                  80
Ser Glu Asn Gly Leu Gln Phe Phe Leu Pro Val Ile Ala Ser Leu Tyr
                85                  90                  95
Leu Gly Ile Ile Val Ala Pro Val Asn Asp Lys Tyr Ile Glu Arg Glu
            100                 105                 110
Leu Ile His Ser Leu Gly Ile Val Lys Pro Arg Ile Val Phe Cys Ser
        115                 120                 125
Lys Asn Thr Phe Gln Lys Val Leu Asn Val Lys Ser Lys Leu Lys Ser
130                 135                 140
Ile Glu Thr Ile Ile Ile Leu Asp Leu Asn Glu Asp Leu Gly Gly Tyr
145                 150                 155                 160
Gln Cys Leu Asn Asn Phe Ile Ser Gln Asn Ser Asp Ser Asn Leu Asp
                165                 170                 175
```

```
Val Lys Lys Phe Lys Pro Tyr Ser Phe Asn Arg Asp Asp Gln Val Ala
            180                 185                 190

Leu Ile Met Phe Ser Ser Gly Thr Thr Gly Leu Pro Lys Gly Val Met
            195                 200                 205

Leu Thr His Lys Asn Ile Val Ala Arg Phe Ser Leu Ala Lys Asp Pro
            210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                    245                 250                 255

Cys Gly Phe Arg Val Val Leu Met His Thr Phe Glu Glu Lys Leu Phe
                260                 265                 270

Leu Gln Ser Leu Gln Asp Tyr Lys Val Glu Ser Thr Leu Leu Val Pro
                275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
                340                 345                 350

Lys Gly Asp Ala Lys Pro Gly Ser Thr Gly Lys Ile Val Pro Phe His
                355                 360                 365

Ala Val Lys Val Val Asp Pro Thr Thr Gly Lys Ile Leu Gly Pro Asn
    370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
                420                 425                 430

Ile Val Asp Arg Leu Lys Ser Leu Ile Lys Tyr Lys Gly Tyr Gln Val
                435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
                500                 505                 510

Gly Gly Val Lys Phe Leu Asp Glu Ile Pro Lys Gly Ser Thr Gly Lys
                515                 520                 525

Ile Asp Arg Ser Val Leu Arg Gln Met Phe Glu Lys His Thr Asn Gly
                530                 535                 540

<210> SEQ ID NO 3
<211> LENGTH: 544
<212> TYPE: PRT
<213> ORGANISM: Photuris pennsylvanica
<220> FEATURE:
<221> NAME/KEY: MISC_FEATURE
<223> OTHER INFORMATION: Mutant luciferase protein LucPpe2m133
```

```
<400> SEQUENCE: 3

Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
            20                  25                  30

Ala Asp Ile Pro Gly Cys Ile Ala Leu Thr Asn Ala His Thr Lys Glu
            35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
                85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
            115                 120                 125

Lys Asn Thr Phe Gln Lys Val Leu Asn Val Lys Ser Lys Leu Lys Ser
130                 135                 140

Ile Glu Thr Ile Ile Ile Leu Asp Leu Asn Asp Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Leu Ile Met Phe Ser Ser Gly Thr Thr Gly Leu Pro Lys Gly Val Met
            195                 200                 205

Leu Thr His Lys Asn Ile Val Ala Arg Phe Ser Ile Ala Lys Asp Pro
210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
            275                 280                 285

Thr Leu Met Ala Phe Leu Ala Lys Ser Ala Leu Val Glu Lys Tyr Asp
290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Gly Asp Ala Lys Pro Gly Ser Thr Gly Lys Ile Val Pro Phe His
            355                 360                 365

Ala Val Lys Val Val Asp Pro Thr Thr Gly Lys Ile Leu Gly Pro Asn
370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415
```

```
Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
            435                 440                 445

Ala Pro Ala Glu Ile Glu Gly Ile Leu Leu Gln His Pro Tyr Ile Val
            450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
            485                 490                 495

Val Gln Asp Tyr Val Ala Ser Gln Val Ser Thr Ala Lys Trp Leu Arg
            500                 505                 510

Gly Gly Val Ile Phe Leu Asp Glu Ile Pro Lys Gly Ser Thr Gly Lys
            515                 520                 525

Ile Asp Arg Ser Val Leu Arg Gln Met Leu Glu Lys His Thr Asn Gly
            530                 535                 540

<210> SEQ ID NO 4
<211> LENGTH: 544
<212> TYPE: PRT
<213> ORGANISM: Photuris pennsylvanica
<220> FEATURE:
<221> NAME/KEY: MISC_FEATURE
<223> OTHER INFORMATION: Mutant luciferase protein LucPpe2m146

<400> SEQUENCE: 4

Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
            20                  25                  30

Ala Ala Ile Pro Gly Cys Ile Ala Leu Thr Asn Ala His Thr Lys Glu
            35                  40                  45

Asn Val Leu Tyr Glu Glu Phe Leu Lys Leu Ser Cys Arg Leu Ala Glu
        50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
            85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
            115                 120                 125

Lys Asn Thr Phe Gln Lys Val Leu Asn Val Lys Ser Lys Leu Lys Ser
        130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
            165                 170                 175

Val Lys Lys Phe Lys Pro Tyr Ser Phe Asn Arg Asp Asp Gln Val Ala
            180                 185                 190

Ser Ile Met Phe Ser Ser Gly Thr Thr Gly Leu Pro Lys Gly Val Met
            195                 200                 205

Leu Thr His Lys Asn Ile Val Ala Arg Phe Ser Ile Ala Lys Asp Pro
        210                 215                 220

Thr Phe Gly Asn Ala Ile Asn Pro Thr Ser Ala Ile Leu Thr Val Ile
```

225                 230                 235                 240
    Pro Phe His His Gly Phe Gly Met Met Thr Thr Leu Gly Tyr Phe Thr
                        245                 250                 255
    Cys Gly Phe Arg Val Val Leu Met His Thr Phe Glu Glu Lys Leu Phe
                        260                 265                 270
    Leu Gln Ser Leu Gln Asp Tyr Lys Val Glu Ser Thr Leu Leu Val Pro
                        275                 280                 285
    Thr Leu Met Ala Phe Leu Ala Lys Ser Ala Leu Val Glu Lys Tyr Asp
            290                 295                 300
    Leu Ser His Leu Lys Glu Ile Ala Ser Gly Gly Ala Pro Leu Ser Lys
    305                 310                 315                 320
    Glu Ile Gly Glu Met Val Lys Lys Arg Phe Lys Leu Asn Phe Val Arg
                        325                 330                 335
    Gln Gly Tyr Gly Leu Thr Glu Thr Thr Ser Ala Val Leu Ile Thr Pro
                        340                 345                 350
    Lys Gly Asp Ala Lys Pro Gly Ser Thr Gly Lys Ile Val Pro Leu His
                        355                 360                 365
    Ala Val Lys Val Val Asp Pro Thr Thr Gly Lys Ile Leu Gly Pro Asn
            370                 375                 380
    Glu Pro Gly Glu Leu Tyr Phe Lys Gly Pro Met Ile Met Lys Gly Tyr
    385                 390                 395                 400
    Tyr Asn Asn Glu Glu Ala Thr Lys Ala Ile Ile Asp Asn Asp Gly Trp
                        405                 410                 415
    Leu Arg Ser Gly Asp Ile Ala Tyr Tyr Asp Asn Asp Gly His Phe Tyr
                        420                 425                 430
    Ile Val Asp Arg Leu Lys Ser Leu Ile Lys Tyr Lys Gly Tyr Gln Val
                        435                 440                 445
    Ala Pro Ala Glu Ile Glu Gly Ile Leu Leu Gln His Pro Tyr Ile Val
            450                 455                 460
    Asp Ala Gly Val Thr Gly Ile Pro Asp Glu Ala Ala Gly Glu Leu Pro
    465                 470                 475                 480
    Ala Ala Gly Val Val Gln Thr Gly Lys Tyr Leu Asn Glu Gln Ile
                        485                 490                 495
    Val Gln Asp Tyr Val Ala Ser Gln Val Ser Thr Ala Lys Trp Leu Arg
                        500                 505                 510
    Gly Gly Val Lys Phe Leu Asp Glu Ile Pro Lys Gly Ser Thr Gly Lys
            515                 520                 525
    Ile Asp Arg Ser Val Leu Arg Gln Met Leu Glu Lys His Thr Asn Gly
    530                 535                 540

<210> SEQ ID NO 5
<211> LENGTH: 1639
<212> TYPE: DNA
<213> ORGANISM: Photuris pennsylvanica
<220> FEATURE:
<221> NAME/KEY: misc_feature
<223> OTHER INFORMATION: Mutant luciferase gene LucPpe2m78

<400> SEQUENCE: 5
ggatccaatg gcagataaga atattttata tgggcccgaa ccatttttatc ccttggctga      60 tgggacggct ggagaacaga tgtttgacgc attatctcgt tatgcagata tttccggatg     120
catagcattg acaaatgctc atacaaaaga aaatgtttta tatgaagagt ttttaaaatt     180
gtcgtgtcgt ttagcggaaa gttttaaaaa gtatggatta aaacaaaacg acacaatagc     240
ggtgtgtagc gaaaatggtt tgcaattttt ccttcctgta attgcatcat gtatcttgg     300

```
aataattgca gcacctgtta gtgataaata cattgaacgt gaattaatac acagtcttgg    360
tattgtaaaa ccacgcataa ttttttgctc caagaatact tttcaaaaag tactgaatgt    420
aaaatctaaa ttaaaatctg tagaaactat tattatatta gacttaaatg aagacttagg    480
aggttatcaa tgcctcaaca actttatttc tcaaaattcc gatagtaatc tggacgtaaa    540
aaaatttaaa ccatattctt ttaatcgaga cgatcaggtt gcgttggtaa tgttttcttc    600
tggtacaact ggtgttccga agggagtcat gctaactcac aagaatattg ttgcacgatt    660
ttctcttgca aagatccta cttttggtaa cgcaattaat cccacgacag caattttaac     720
ggtaatacct ttccaccatg gttttggtat gatgaccaca ttaggatact ttacttgtgg    780
attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg   1020
gtatggatta acagaaacca cttcggctgt tttaattaca ccgaaaggtg acgccagacc   1080
gggatcaact ggtaaaatag taccatttca cgctgttaaa gttgtcgatc ctacaacagg   1140
aaaaattttg gggccaaatg aacctggaga attgtatttt aaaggcgcca tgataatgaa   1200
gggttattat aataatgaag aagctactaa agcaattatt gataatgacg gatggttgcg   1260
ctctggtgat attgcttatt atgacaatga tggccatttt tatattgtgg acaggctgaa   1320
gtcattaatt aaatataaag gttatcaggt tgcacctgct gaaattgagg gaatactctt   1380
acaacatccg tatattgttg atgccggcgt tactggtata ccggatgaag ccgcgggcga   1440
gcttccagct gcaggtgttg tagtacagac tggaaaatat ctaaacgaac aaatcgtaca   1500
agattttgtt tccagtcaag tttcaacagc caaatggcta cgtggtgggg tgaaattttt   1560
ggatgaaatt cccaaaggat caactggaaa aattgacaga aagtgttaa gacaaatgtt    1620 tgaaaaacac accaatggg                                                 1639
```

<210> SEQ ID NO 6
<211> LENGTH: 1639
<212> TYPE: DNA
<213> ORGANISM: Photuris pennsylvanica
<220> FEATURE:
<221> NAME/KEY: misc_feature
<223> OTHER INFORMATION: Mutant luciferase gene LucPpe2m90

<400> SEQUENCE: 6

```
ggatccaatg gcagataaga atattttata tgggcccgaa ccatttttatc ccttggaaga    60 tgggacggct ggagaacaga tgtttgacgc attatctcgt tatgcagata ttccgggctg   120
catagcattg acaaatgctc atacaaaaga aaatgtttta tatgaagagt ttctgaaact   180
gtcgtgtcgt ttagcggaaa gttttaaaaa gtatggatta aaacaaaacg acacaatagc   240
ggtgtgtagc gaaaatggtc tgcaattttt ccttcctgta attgcatcat gtatcttgg    300 aataattgtg gcacctgtta acgataaata cattgaacgt gaattaatac acagtcttgg   360
tattgtaaaa ccacgcatag ttttttgctc caagaatact tttcaaaaag tactgaatgt   420
aaaatctaaa ttaaaatcta ttgaaactat tattatatta gacttaaatg aagacttagg   480
aggttatcaa tgcctcaaca actttatttc tcaaaattcc gatagtaatc tggacgtaaa   540
aaaatttaaa ccatattctt ttaatcgaga cgatcaggtt gcgttgatta tgttttcttc   600
tggtacaact ggtctgccga agggagtcat gctaactcac aagaatattg ttgcacgatt   660
```

```
ttctcttgca aaagatccta cttttggtaa cgcaattaat cccacgacag caattttaac    720
ggtaatacct ttccaccatg gttttggtat gatgaccaca ttaggatact ttacttgtgg    780
attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg   1020
gtatggatta acagaaacca cttcggctgt tttaattaca ccgaaaggtg acgccaaacc   1080
gggatcaact ggtaaaatag taccatttca cgctgttaaa gttgtcgatc ctacaacagg   1140
aaaaattttg gggccaaatg aacctggaga attgtatttt aaaggcccga tgataatgaa   1200
gggttattat aataatgaag aagctactaa agcaattatt gataatgacg gatggttgcg   1260
ctctggtgat attgcttatt atgacaatga tggccatttt tatattgtgg acaggctgaa   1320
gtcactgatt aaatataaag gttatcaggt tgcacctgct gaaattgagg gaatactctt   1380
acaacatccg tatattgttg atgccggcgt tactggtata ccggatgaag ccgcgggcga   1440
gcttccagct gcaggtgttg tagtacagac tggaaaatat ctaaacgaac aaatcgtaca   1500
agattatgtt gccagtcaag tttcaacagc caaatggcta cgtggtgggg tgaaattttt   1560
ggatgaaatt cccaaaggat caactggaaa aattgacaga aagtgttaa gacaaatgtt   1620 tgaaaaacac accaatggg                                                1639

<210> SEQ ID NO 7
<211> LENGTH: 1639
<212> TYPE: DNA
<213> ORGANISM: Photuris pennsylvanica
<220> FEATURE:
<221> NAME/KEY: misc_feature
<223> OTHER INFORMATION: Mutant luciferase gene LucPpe2m133

<400> SEQUENCE: 7
agatccaatg gcagataaga atattttata tgggcccgaa ccatttatc ccttggaaga     60 tgggacggct ggagaacaga tgtttgacgc attatctcgt tatgcagata ttccgggctg    120
catagcattg acaaatgctc atacaaaaga aaatgtttta tatgaagagt ttctgaaact    180
gtcgtgtcgt ttagcggaaa gttttaaaaa gtatggatta aaacaaaacg acacaatagc    240
ggtgtgtagc gaaaatagtc tgcaattttt ccttcctgta attgcatcat gtatcttgg     300 aataattgtg gcacctgtta acgataaata cattgaacgt gaattaatac acagtcttgg    360
tattgtaaaa ccacgcatag ttttttgctc caagaatact tttcaaaaag tactgaatgt    420
aaaatctaaa ttaaatccta ttgaaactat tattatatta gacttaaatg atgacttagg    480
aggttatcaa tgcctcaaca actttatttc tcaaaattcc gatagtaatc tggacgtaaa    540
aaaatttaaa ccatattctt ttaatcgaga cgatcaggtt gcgttgatta tgttttcttc    600
tggtacaact ggtctgccga agggagtcat gctaactcac aagaatattg ttgcacgatt    660
ttctattgca aaagatccta cttttggtaa cgcaattaat cccacgtcag caattttaac    720
ggtaatacct ttccaccatg gttttggtat gatgaccaca ttaggatact ttacttgtgg    780
attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg   1020
```

```
gtatggatta acagaaacca cttcggctgt tttaattaca ccgaaaggtg acgccaaacc    1080
gggatcaact ggtaaaatag taccatttca cgctgttaaa gttgtcgatc ctacaacagg    1140
aaaaattttg gggccaaatg aacctggaga attgtatttt aaaggcccga tgataatgaa    1200
gggttattat aataatgaag aagctactaa agcaattatt gataatgacg gatggttgcg    1260
ctctggtgat attgcttatt atgacaatga tggccatttt tatattgtgg acaggctgaa    1320
gtcactgatt aaatataaag gttatcaggt tgcacctgct gaaattgagg gaatactctt    1380
acaacatccg tatattgttg atgccggcgt tactggtata ccggatgaag ccgcgggcga    1440
gcttccagct gcaggtgttg tagtacgact ggaaaatat ctaaacgaac aaatcgtaca    1500
agattatgtt gccagtcaag tttcaacagc caaatggcta cgtggtgggg tgatattttt    1560
ggatgaaatt cccaaaggat caactggaaa aattgacaga aagtgttaa gacaaatgtt    1620 agaaaaacac accaatggg                                                1639
```

<210> SEQ ID NO 8
<211> LENGTH: 1639
<212> TYPE: DNA
<213> ORGANISM: Photuris pennsylvanica
<220> FEATURE:
<221> NAME/KEY: misc_feature
<223> OTHER INFORMATION: Mutant luciferase gene LucPpe2m146

<400> SEQUENCE: 8

```
ggatccaatg gcagataaga atattttata tgggcccgaa ccatttttatc ccttggaaga     60 tgggacggct ggagaacaga tgtttgacgc attatctcgt tatgcagcta ttccgggctg    120
catagcattg acaaatgctc atacaaaaga aaatgttttta tatgaagagt ttctgaaact    180
gtcgtgtcgt ttagcggaaa gttttaaaaa gtatggatta aaacaaaacg acacaatagc    240
ggtgtgtagc gaaaatagtc tgcaattttt ccttcctgta attgcatcat tgtatcttgg    300
aataattgtg gcacctgtta acgataaata cattgaacgt gaattaatac acagtcttgg    360
tattgtaaaa ccacgcatag ttttttgctc caagaatact tttcaaaaag tactgaatgt    420
aaaatctaaa ttaaaatcta ttgaaactat tattatatta gacttaaatg aagacttagg    480
aggttatcaa tgcctcaaca actttatttc tcaaaattcc gatagtaatc tggacgtaaa    540
aaaatttaaa ccctattctt ttaatcgaga cgatacaggt tcgtcgatta tgttttcttc    600
tggtacaact ggtctgccga agggagtcat gctaactcac aagaatattg ttgcacgatt    660
ttctattgca aaagatccta cttttggtaa cgcaattaat cccacgtcag caattttaac    720
ggtaatacct ttccaccatg gttttggtat gatgaccaca ttaggatact tacttgtgg    780 attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcacccttt    960 atcaaaagaa attggggaga tggtgaaaaa acggtttaaa ttaaactttg tcaggcaagg    1020
gtatggatta acagaaacca cttcggctgt tttaattaca ccgaaaggtg acgccaaacc    1080
gggatcaact ggtaaaatag taccattcca cgctgttaaa gttgtcgatc ctacaacagg    1140
aaaaattttg gggccaaatg aacctggaga attgtatttt aaaggcccga tgataatgaa    1200
gggttattat aataatgaag aagctactaa agcaattatt gataatgacg gatggttgcg    1260
ctctggtgat attgcttatt atgacaatga tggccatttt tatattgtgg acaggctgaa    1320
gtcactgatt aaatataaag gttatcaggt tgcacctgct gaaattgagg gaatactctt    1380
```

```
acaacatccg tatattgttg atgccggcgt tactggtata ccggatgaag ccgcgggcga    1440
gcttccagct gcaggtgttg tagtacagac tggaaaatat ctaaacgaac aaatcgtaca    1500
agattatgtt gccagtcaag tttcaacagc caaatggcta cgtggtgggg tgaaattttt    1560
ggatgaaatt cccaaaggat caactggaaa aattgacaga aaagtgttaa gacaaatgtt    1620
agaaaaacac accaatggg                                                 1639
```